(12) United States Patent
Dufresne et al.

(10) Patent No.: US 7,163,932 B2
(45) Date of Patent: Jan. 16, 2007

(54) ARYLDIFLUOROMETHYLPHOSPHONIC ACIDS FOR TREATMENT OF DIABETES

(75) Inventors: Claude Dufresne, Dollard-des-Ormeaux (CA); Yves Leblanc, Kirkland (CA); Cheuk K. Lau, Ile Bizard (CA); Patrick Roy, Dollard des Ormeaux (CA); Chun Sing Li, Dollard-des-Ormeaux (CA)

(73) Assignee: Merck Frosst Canada & Co., Kirkland (CA)

( * ) Notice: Subject to any disclaimer, the term of this patent is extended or adjusted under 35 U.S.C. 154(b) by 484 days.

(21) Appl. No.: 10/481,485

(22) PCT Filed: Jun. 19, 2002

(86) PCT No.: PCT/CA02/00923

§ 371 (c)(1),
(2), (4) Date: Dec. 18, 2003

(87) PCT Pub. No.: WO02/102813

PCT Pub. Date: Dec. 27, 2002

(65) Prior Publication Data

US 2004/0176330 A1    Sep. 9, 2004

Related U.S. Application Data

(60) Provisional application No. 60/299,504, filed on Jun. 20, 2001.

(51) Int. Cl.
*A61K 31/66* (2006.01)
*C07F 9/22* (2006.01)
(52) U.S. Cl. ............................................. 514/75; 562/8
(58) Field of Classification Search ................... 514/75; 562/8
See application file for complete search history.

(56) References Cited

U.S. PATENT DOCUMENTS

| 6,448,429 B1 | 9/2002 | Leblanc et al. | |
| 6,465,444 B1 | 10/2002 | Bayly et al. | |
| 6,486,141 B1 | 11/2002 | Lau et al. | |
| 6,583,126 B1 | 6/2003 | Leblanc et al. | |
| 6,716,825 B1 * | 4/2004 | Hostetler et al. | 514/52 |
| 7,001,896 B1 * | 2/2006 | Yin et al. | 514/119 |

FOREIGN PATENT DOCUMENTS

| WO | WO 0017211 | 3/2000 |
| WO | WO 0146206 | 6/2001 |
| WO | WO 0170753 | 9/2001 |

* cited by examiner

*Primary Examiner*—Deborah C. Lambkin
(74) *Attorney, Agent, or Firm*—James L. McGinnus; Melvin Winokur

(57) ABSTRACT

The invention encompasses the novel class of compounds represented by the formula below, which are inhibitors of the PTP-1B enzyme.

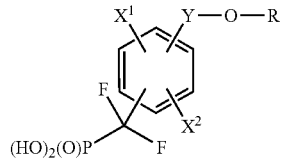

The invention also encompasses pharmaceutical compositions which include the compounds shown above and methods of treating or preventing PTP-1B mediated diseases, including diabetes.

19 Claims, No Drawings

ARYLDIFLUOROMETHYLPHOSPHONIC ACIDS FOR TREATMENT OF DIABETES

CROSS REFERENCE TO RELATED APPLICATIONS

This application is a U.S. National Phase application under 35 U.S.C. § 371 of PCT Application No. PCT/CA02/00923, filed Jun. 19, 2002, and claims priority under 35 U.S.C. § 119 (e) from U.S. Application No. 60/299,504, filed Jun. 20, 2001.

FIELD OF THE INVENTION

This invention relates to a novel class of phosphonic acid derivatives that are inhibitors of PTP-1B and that may be advantageous in the treatment of Type II diabetes and other PTP-1B mediated diseases.

BACKGROUND OF THE INVENTION

Protein tyrosine phosphatases are a large family of trans-membrane or intracellular enzymes that dephosphorylate substrates involved in a variety of regulatory processes (Fischer et al., 1991, Science 253:401–406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252–5256; Goldstein, 1993, Receptor 3:1–15).

Determining which proteins are substrates of PTP-1B has been of considerable interest. One substrate which has aroused especial interest is the insulin receptor. The binding of insulin to its receptor results in autophosphorylation of the receptor, most notably on tyrosines 1146, 1150, and 1151 in the kinase catalytic domain (White & Kahn, 1994, J. Biol. Chem. 269:1–4). This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379–1385 ("Seely") studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503–20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Recently, Kennedy et al., 1999, Science 283: 1544–1548 showed that protein tyrosine phosphatase PTP-1B is a negative regulator of the insulin signalling pathway, suggesting that inhibitors of this enzyme may be beneficial in the treatment of Type 2 diabetes. Mice lacking PTP-1B are resistant to both diabetes and obesity.

Thus, inhibitors of PTP-1B may improve insulin-sensitivity. They may have utility in controlling or treating Type 1 and Type 2 diabetes, in improving glucose tolerance, and in improving insulin sensitivity in patients in need thereof. The compounds may also be useful in treating or preventing cancer, neurodegenerative diseases and the like. PTP-1B inhibitors are not currently used in any medications, and new compounds are needed to find compounds that are suitable for medicinal uses

SUMMARY OF THE INVENTION

Compounds represented by formula I, including pharmaceutically acceptable salts thereof, and prodrugs thereof, are PTP-1B inhibitors that may be useful in the treatment of diabetes and related medical conditions, and may also be useful in the treatment of other PTP-1B mediated diseases or conditions.

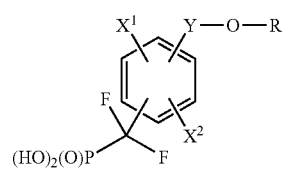

In the compounds of formula I:

$X^1$ is selected from the group consisting of: halogen, CN, $CO_2H$, $CO_2C_{1-6}$alkyl, $CO_2C_{2-6}$alkenyl, $OC_{1-6}$alkyl, $OC_{2-6}$alkenyl, $C(O)C_{1-6}$alkyl, $C(O)C_{2-6}$alkenyl, $OC(O)C_{1-6}$alkyl, $OC(O)C_{2-6}$alkenyl, $C_{1-6}$ alkyl, $C_{2-6}$alkenyl, $S(O)_2NR^1R^2$, $C(O)NR^1R^2$, and $NR^1R^2$, wherein each alkyl group and each alkenyl group in each substituent is optionally substituted with 1–7 groups independently selected from (a) 1–5 halogen atoms and (b) 1–2 substituents independently selected from $OC_{1-3}$alkyl, $C(O)C_{1-3}$alkyl, $OC(O)C_{1-3}$alkyl, $CO_2H$, and $CO_2C_{1-3}$alkyl;

$X^2$ is selected from the group consisting of: H, OH, halogen, CN, $CO_2H$, $CO_2C_{1-6}$alkyl, $CO_2C_{2-6}$alkenyl, $OC_{1-6}$alkyl, $OC_{2-6}$alkenyl, $C(O)C_{1-6}$alkyl, $C(O)C_{2-6}$alkenyl, $OC(O)C_{1-6}$alkyl, $OC(O)C_{2-6}$alkenyl, $C_{1-6}$ alkyl, $C_{2-6}$alkenyl, $S(O)_2NR^1R^2$, $C(O)NR^1R^2$, and $NR^1R^2$, wherein each alkyl group and each alkenyl group in each substituent is optionally substituted with 1–7 groups independently selected from (a) 1–5 halogen atoms and (b) 1–2 substituents independently selected from $OC_{1-3}$alkyl, $C(O)C_{1-3}$alkyl, $OC(O)C_{1-3}$alkyl, $CO_2H$, and $CO_2C_{1-3}$alkyl;

$R^1$ and $R^2$ are each independently selected from the group consisting of H and $C_{1-6}$alkyl, wherein said alkyl substituents are optionally substituted with 1–5 halogen atoms;

Alkyl, alkenyl, alkadienyl and alkynyl are linear or branched hydrocarbon structures, except where otherwise defined, containing the indicated number of carbon atoms and being substituted as indicated;

$X^1$, $X^2$, $CF_2P(O)(OH)_2$ and Y—O—R are each substituted onto any position of the aromatic ring;

Y is a $C_{1-4}$ alkylene group, wherein said alkylene group is linear and optionally has one double bond or one triple bond connecting two adjacent carbon atoms, wherein each carbon of said $C_{1-4}$alkylene group independently may have one optional substituent independently selected from the group consisting of $C_{1-4}$alkyl, $C_{2-4}$alkenyl, $C_{2-4}$alkynyl, and halogen, said $C_{1-4}$alkyl, $C_{2-4}$alkenyl, and $C_{2-4}$alkynyl substituents being optionally substituted with 1–3 halogens;

R is selected from H, $C_{1-6}$ alkyl, and an aromatic group selected from phenyl, naphthyl, and biphenyl, wherein $C_{1-6}$alkyl is linear and optionally has one double bond, one triple bond or one S atom connecting two adjacent carbon atoms, wherein each carbon of said $C_{1-6}$alkyl group independently may have one optional substituent selected from the group consisting of $C_{1-4}$alkyl, $C_{2-4}$alkenyl, $C_{2-4}$alkynyl, halogen, phenyl, naphthyl, biphenyl and phthalimide, said $C_{1-4}$alkyl, $C_{2-4}$alkenyl, and $C_{2-4}$alkynyl substituents being optionally substituted with 1–4 substituents independently selected from 1–3 halogens and one aromatic group selected from phenyl, naphthyl, and biphenyl, wherein R comprises 0–2 aromatic substituents, wherein said aromatic substituents optionally may be substituted onto the same carbon atom of alkyl, alkenyl and alkynyl when there are two aromatic substituents, and wherein said 0–2 aromatic groups that are substituents on R when R is $C_{1-6}$ alkyl are optionally substituted with 1–5 substituents independently selected from halogen, $C_{1-4}$alkyl, $C_{2-4}$alkenyl, $C_{2-4}$alkynyl, $OC_{1-4}$alkyl, $OC_{2-4}$alkenyl, $OC_{2-4}$alkynyl, phenoxy, $CO_2H$, $CO_2C_{1-4}$alkyl, $SC_{1-4}$alkyl, $S(O)C_{1-4}$alkyl, $S(O)_2C_{1-4}$alkyl, $NO_2$ and CN, wherein said alkyl, alkenyl, alkynyl, Oalkyl, Oalkenyl, Oalkynyl and phenoxy substituents are optionally substituted with 1–5 halogens, and wherein when R is an aromatic group, said aromatic group is optionally substituted with 1–5 substituents selected from halogen, $C_{1-4}$alkyl, $C_{2-4}$alkenyl, $C_{2-4}$alkynyl, $OC_{1-4}$alkyl, $OC_{2-4}$alkenyl, $OC_{2-4}$alkynyl, phenoxy, $CO_2H$, $CO_2C_{1-4}$alkyl, $SC_{1-4}$alkyl, $S(O)C_{1-4}$alkyl, $S(O)_2C_{1-4}$alkyl, $NO_2$ and CN, wherein said alkyl, alkenyl, alkynyl, Oalkyl, Oalkenyl, Oalkynyl and phenoxy substituents are optionally substituted with 1–5 halogens.

Methods of treating and controlling diabetes, obesity, and other diseases and conditions using the compounds of Formula I are taught herein. Pharmaceutical compositions and combination treatments are also disclosed herein.

DETAILED DESCRIPTION OF THE INVENTION

The compounds of Formula I have numerous embodiments, as summarized below:

One embodiment comprises compounds having Formula I wherein $X^1$ is ortho to the group $CF_2PO(OH)_2$ and is selected from the group consisting of Cl, Br, $CH_3$, $OCH_3$, $CF_3$, $OCF_3$, and OH, and $X^2$ is selected from the group consisting of H, Cl, Br, $CH_3$, $OCH_3$, $CF_3$, $OCF_3$, and OH In preferred embodiments, $X^1$ is Br and $X^2$ is H.

In preferred embodiments, Y is $CH_2$.

In highly preferred compounds, $X^1$ is Br;

$X^2$ is H;

Y is $CH_2$; and $X^1$ is ortho to $CF_2PO(OH)_2$.

In other preferred embodiments, R is selected from $C_{1-6}$alkyl and phenyl, wherein phenyl is optionally substituted with 1–3 halogens, wherein $C_{1-6}$alkyl is linear and optionally has one double bond, one triple bond or one S atom connecting two adjacent carbon atoms, wherein $C_{1-6}$alkyl is optionally substituted with 1–2 groups independently selected from phenyl, phthalimide, naphthyl and biphenyl, wherein phenyl, naphthyl, phthalimide, and biphenyl are optionally substituted with 1–3 groups independently selected from halogen, $C_{1-6}$alkyl, phenyl, phenoxy, $SC_{1-4}$alkyl, $S(O)_2C_{1-4}$alkyl, $NO_2$, and $CO_2C_{1-4}$alkyl, wherein $C_{1-6}$alkyl, $SC_{1-4}$alkyl, $S(O)_2C_{1-4}$alkyl, and $CO_2C_{1-4}$alkyl are linear or branched and are optionally substituted with 1–3 halogens.

In other highly preferred compounds, $X^1$ is Br and is ortho to $CF_2PO(OH)_2$;

$X^2$ is H;

Y is $CH_2$; and

R is selected from phenyl and $C_{1-3}$alkyl, wherein phenyl is optionally substituted with 1–3 halogens, and $C_{1-3}$alkyl is linear and optionally has one double bond, one triple bond or one S atom connecting two adjacent carbon atoms, wherein $C_{1-3}$alkyl is optionally substituted with 1–2 groups independently selected from phenyl, phthalimide, naphthyl and biphenyl, wherein phenyl, naphthyl, phthalimide, and biphenyl are optionally substituted with 1–3 groups independently selected from halogen, $C_{1-6}$alkyl, phenyl, phenoxy, $SC_{1-4}$alkyl, $S(O)_2C_{1-4}$alkyl, $NO_2$, and $CO_2C_{1-4}$alkyl, wherein $C_{1-6}$alkyl, $SC_{1-4}$alkyl, $S(O)_2C_{1-4}$alkyl, and $CO_2C_{1-4}$alkyl are linear or branched and are optionally substituted with 1–3 halogens.

The invention also comprises prodrugs of the compounds of Formula I. In these, one or more of $R^5$ is a moiety that is converted to H under physiological conditions during or after administration to a mammalian patient, and the remainder of $R^5$ moieties are H or pharmaceutically acceptable salts therof. Conversion of the prodrug, as by hydrolysis or metabolism, yields a compound having Formula I, where $R^5$ is H, or a pharmaceutically acceptable salt thereof. Prodrugs are described in more detail below.

Specific compounds having formula I are shown in Table 1. Synthetic schemes for making these compounds are provided, and specific syntheses of exemplified compounds are also provided.

Methods of treating, preventing, or controlling diabetes and other diseases using the compounds of Formula I are disclosed herein. A method of treating, controlling or preventing diabetes and complications thereof in a mammalian patient in need of such treatment includes administering to the patient an anti-diabetic effective amount of a compound of Formula I. A method of treating, controlling or preventing obesity in a mammalian patient in need of such treatment comprises the administration to the patient an anti-obesity effective amount of a compound in accordance with claim 1. Such methods also include the administration of a second compound, which may be an anti-diabetic compound, an anti-obesity compound, or an HMG-CoA reductase inhibitor, in an amount effective to treat, control or prevent diabetes or obesity, or to improve a poor lipid profile.

A method of treating, controlling or preventing atherosclerosis in a mammalian patient in need of such treatment comprises administering to the patient an effective amount of a compound of Formula I and an effective amount of an HMG-CoA reductase inhibitor.

More generally, compounds of Formula I may be used as the active compound in a method for treating, preventing, or controlling one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease. The method comprises the administration of an effective amount of the compound of Formula I. Combination treatments can also be used, in which case, the method comprises the administration of a compound of Formula I and an effective amount of one or more pharmaceutically active compounds selected from the group consisting of an HMG-CoA reductase inhibitor, an anti-obesity agent, and an antidiabetic compound.

Pharmaceutical compositions also can be made using the compounds of Formula I. Such compositions contain an effective amount of a compound of Formula I in combination with a pharmaceutically acceptable carrier. These compositions are suitable for the treatment, prevention or control of one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease Such pharmaceutical compositions may also include a second anti-diabetic agent or an anti-obesity agent. They may also include a cholesterol lowering agent. Pharmaceutical compositions may therefore include: (1) an effective amount of a compound of Formula I, (2) an effective amount of one or more pharmaceutically active compounds selected from the group consisting of an HMG-CoA reductase inhibitor, an anti-obesity agent, and an anti-diabetic agent, and (3) a pharmaceutically acceptable carrier.

Such pharmaceutical compositions that contain a second active compound or component and that are suitable for the treatment, prevention or control of one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, may be comprised of the following:

(1) an effective amount of a compound of Formula 1;
(2) an effective amount of one or more pharmaceutically active compounds listed below; and
(3) a pharmaceutically acceptable carrier; where the pharmaceutically active compounds are selected from the group consisting of:
   (a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; and (ii) biguanides such as metformin and phenformin;
   (b) insulin or insulin mimetics;
   (c) sulfonylureas such as tolbutamide and glipizide, or related materials;
   (d) α-glucosidase inhibitors (such as acarbose);
   (e) cholesterol lowering agents such as (i) HMG-CoA reductase inhibitors (lovastatin, simvastatin, pravastatin, fluvastatin, atorvastatin, rivastatin and other statins), (ii) sequestrants (cholestyramine, colestipol and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) inhibitors of cholesterol absorption, for example beta-sitosterol and acyl CoA:cholesterol acyltransferase inhibitors, for example melinamide, and (vi) probucol;
   (f) PPARα/γ agonists;
   (g) antiobesity compounds such as appetite suppressants, fenfluramine, dexfenfluramine, phentiramine, subitramine, orlistat, neuropeptide Y5 inhibitors (NP Y5 receptor antagonosts), leptin, which is a peptidic hormone, β₃ adrenergic receptor agonists, and PPARγ antagonists and partial agonists;
   (h) ileal bile acid transporter inhibitors; and
   (i) insulin receptor activators.

The pharmaceutically active compounds that can be used as the second component in the combination pharmaceutical compositions described above may be summarized as:
   (a) insulin sensitizers, PPAR-gamma agonists, partial agonists, and antagonists, PPAR-alpha agonists, PPAR-delta agonists, and biguanides;
   (b) insulin and insulin mimetics;
   (c) sulfonylureas;
   (d) α-glucosidase inhibitors;
   (e) cholesterol lowering agents selected from the group consisting of (i) HMG-CoA reductase inhibitors; (ii) sequestrants, (iii) nicotinyl alcohol, nicotinic acid and salts thereof, (iv) PPARα agonists, (v) inhibitors of cholesterol absorption; and (vi) probucol;
   (f) PPARα/γ agonists;
   (g) antiobesity compounds selected from the group consisting of appetite suppressants, fenfluramine, dexfenfluramine, phentiramine, subitramine, orlistat, neuropeptide Y5 inhibitors (NP Y5 receptor antagonosts), leptin, β₃ adrenergic receptor agonists, and PPARγ antagonists and partial agonists;
   (h) ileal bile acid transporter inhibitors; and
   (i) insulin receptor activators.

Abbreviations

The Following Abbreviations have the Indicated Meanings:

Ac=acetyl
AIBN=2.2-azobisisobutyronitrile
DAST=diethylamino sulfur trifluoride
DMF=N,N-dimethylformamide
DMSO=dimethyl sulfoxide
Et$_3$N=triethylamine
Et$_3$SiH=triethylsilane
HBSS=Hanks balanced salt solution
HEPES=N$^1$-[2-Hydroxyethyl]piperazine-N$^4$-[2-ethanesulfonic acid]
KHMDS=potassium hexamethyldisilazide
LDA=lithium diisopropylamide
LHMDS=lithium hexamethyldisilazide
NBS=N-bromosuccinimide
NMO=4-methylmorpholine N-oxide
Oxone®=potassium peroxymonosulfate
Pd$_2$(dba)$_3$=tris(dibenzylideneacetone)dipalladium(0)
Ph$_3$P=triphenylphosphine
PTP=protein tyrosine phosphatase
r.t.=room temperature
rac.=racemic
Tf=trifluoromethanesulfonyl=triflyl
TFA=trifluoroacetic acid
TFAA=trifluoroacetic anhydride
TfO=trifluoromethanesulfonate=triflate
THF=tetrahydrofuran
TLC=thin layer chromatography
TMSBr=bromotrimethylsilane
Tz=1H (or 2H)-tetrazol-5-yl Alkyl Group Abbreviations Me=methyl
Et=ethyl
n-Pr=normal propyl
i-Pr=isopropyl n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Dose Abbreviations
bid=bis in die=twice daily
qid=quater in die=four times a day
tid=ter in die=three times a day

DEFINITIONS

Alkyl means linear and branched structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl and 3,7-diethyl-2,2-dimethyl-4-propylnonyl. Cycloalkyl means saturated cyclic structures, such as cyclopropyl, cyclopentyl, cycloheptyl, cyclopropylmethyl, methylcyclopropy, adamantyl, cyclododecylmethyl, 2-ethyl-1-bicyclo[4.4.0]decyl and the like.

Fluoroalkyl means alkyl groups of the indicated number of carbon atoms in which one or more hydrogens is replaced by fluorine. Examples are —$CF_3$, —$CH_2CH_2F$, —$CH_2CF_3$, c-Pr-$F_5$, c-Hex-$F_{11}$ and the like. Haloalkyl has the analogous meaning for replacement of one or more hydrogen atoms with any halogen (Cl, Br, F, and/or I).

Alkenyl means linear and branched structures, and combinations thereof containing a double bond with the indicated number of carbon atoms. Examples of alkenyl groups include allyl, 2-butenyl, 3-butenyl, 2-pentenyl, and 1-pentenyl. Cycloalkenyl means cyclic structures having a double bond, such as 2-cyclopentenyl, 3-cyclopentenyl, 2-methylcyclohexenyl, 2-cyclohexenyl, 3-cyclohexenyl and the like. Alkadienyl means the diunsaturated counterpart to alkenyl.

Alkynyl means linear, branched and cyclic structures, and combinations thereof containing a triple bond with the indicated number of carbon atoms. Examples of alkynyl groups include propargyl, 2-butynyl, 3-butynyl and 2-pentynyl.

Alkylene, alkenylene, alkynylene, fluoroalkylene, alkadienylene, and the like, where the suffix "ene" has been added to the name of the monovalent radicals alkyl, alkenyl, alkynyl, fluoroalkyl, alkadienyl, and the like, describe divalent radicals that are the same as their monovalent counterparts, except that two hydrogen atoms rather than one are absent so that the radical will have two points of attachment, in addition to attachments to substituents which may also be present.

Aryl groups include 6–14 membered carbocyclic aromatic ring systems comprising 1–3 phenyl rings. If two or more aromatic rings are present, then the rings are fused together, so that adjacent rings share a common side. Examples are benzene, naphthalene, anthracene and phenanthrene. Preferred aryl groups are benzene and naphthalene. Benzene is most preferred. Substitutions on these are defined herein.

Heteroaryl as used herein represents a 5–10 membered aromatic ring system comprising one ring or two fused rings, 1–4 heteroatoms selected from the groups consisting of N, O, S(O)x, and mixtures thereof wherein x is 0, 1 or 2, and 0–2 carbonyl groups. Carbonyl groups, when present, are not counted as heteroatoms. Heteroaryl includes, but is not limited to, furanyl, diazinyl, imidazolyl, isoxazolyl, isothiazolyl, oxadiazolyl, oxazolyl, pyrazolyl, pyridyl, pyrrolyl, tetrazinyl, thiazolyl, thienyl, triazinyl, triazolyl, 1H-pyrrole-2,5-dionyl, 2-pyrone, 4-pyrone, pyrrolopyridine, furopyridine and thienopyridine. Heteroaryl also includes benzoheteroaryl, defined below. Preferred heteroaryl substituents include quinoline, thiazole, tetrazole, pyridine, imidazole, isoxazole, isothiazole, oxazole, pyrazole, thiophene, oxadiazole, benzothiophene, benzothiazole, benzotriazole, benzothiadiazole, and isoquinoline.

Benzoheteroaryl is a subset of heteroaryl and includes aromatic ring systems containing one or more heteroatoms which also have a fused 6-membered benzene ring, such as 2H-1-benzopyran-2-one, 4H-1-benzopyran-4-one, 2(3H) benzofuranone, 3(2H)benzofuranone, 2,3-dihydrobenzofuran, 2,3-dihydrobenzothiophene, indole, benzofuran, benzothiophene, benzimidazole, benzoxazole, benzothiazole, benzotriazole, benzothiadiazole, 1H-isoindole-1,3(2H)-dione, quinoline, and isoquinoline.

Another subset of heteroaryls includes 5-membered heteroaryls, such as the following:

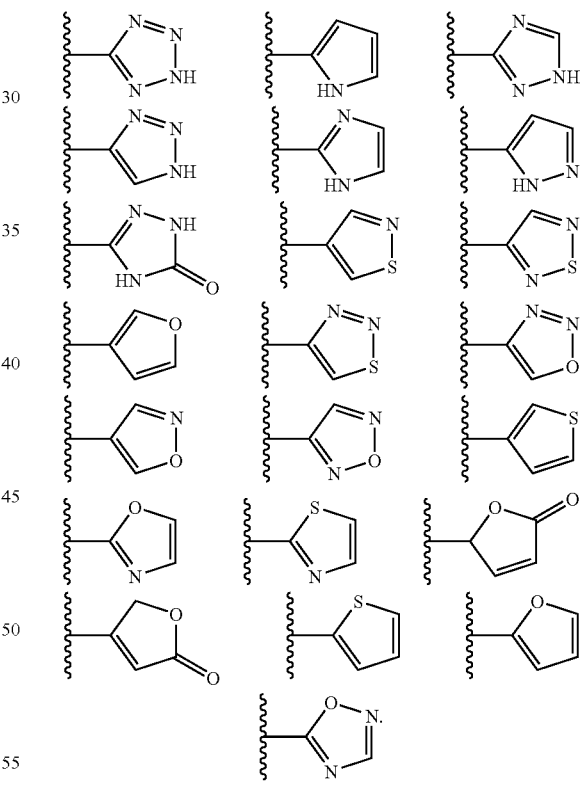

When a heteroaromatic ring is specified as optionally having one or more heteroatoms, this means that at least one heteroatom is present, selected from O, S, SO, $SO_2$ and N, and up to 4 such heteroatoms may be present, depending upon the size of the ring specified. When SO or $S(O)_2$ is in a heteroaromatic ring, generally the S is part of the actual ring structure, and the O atoms are attached to the S but are exocyclic to the actual ring structure.

When a substituent is specified as being optional, then that substituent may be either present or absent. When a list of possible choices is provided for a given substituent, and the substituent is used more than once, then the selection for each use of the substituent in each position is independent of other selections, unless the definition specifically says otherwise.

Metabolites—Prodrugs

Metabolites of the compounds of this invention that are therapeutically active and that are described by formula I also are within the scope of the claimed invention, as are prodrugs, which are compounds that are converted to the claimed active compounds or to salts of the claimed active compounds after they have been administered to a patient. A non-limiting example of a prodrug of the phosphonic acids of this invention would be a monoester or diester of one or more phosphonic acid groups, where the ester functionality preferably has a structure that makes it easily hydrolyzed or metabolized after administration to a patient. Examples of prodrugs include $C_{1-6}$ alkyl esters of the phosphonic acids. Prodrugs that have structures that are more easily hydrolyzed or metabolized are generally more preferred. Examples are illustrated by the structures below, where R'=H or a $C_{1-6}$ alkyl group, and R"=$C_{1-6}$ alkyl group or —O$C_{1-6}$ alkyl group, and Q is the residue of the molecule that is attached to the —$CF_2PO_3H_2$ or —$PO_3H_2$ group in formula I. The alkyl groups and alkoxy groups may optionally be substituted with one or more substituents independently selected from 1–5 halogen atoms, a phenyl group, or a mixture of these. The phenyl group, if present, may optionally be substituted with 1–3 substituents independently selected from halogen, —$CH_3$, —$CF_3$, —$OCH_3$ and —$OCF_3$. In these compounds, and as defined in general throughout this application, the alkyl groups and the alkyl portions of Oalkyl groups may be linear or branched and may optionally be cycloalkyl or may include a cycloalkyl group in their structure. For examples of prodrug structures related to those shown below, see D. N. Srinivasta et al., Bioorganic Chemistry 12, 118–129 (1984).

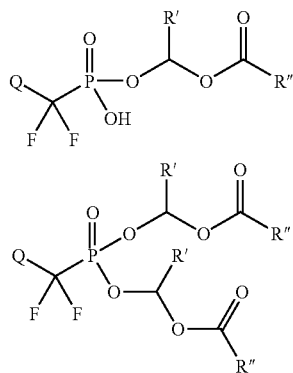

Other ester functionalities that may be used in the monoester or diester phosphonate prodrugs include phenyl esters and benzyl esters, where the phenyl ester groups have the structure -Ophenyl, and the benzyl ester groups have the structure —OCHR'phenyl, in which R' is H or $C_{1-6}$alkyl, and $C_{1-6}$alkyl is substituted as described above. In either case, phenyl is substituted as described above.

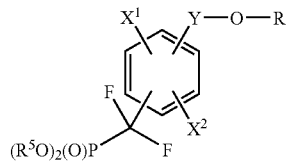

The prodrugs of this invention may therefore be defined as compounds having the formula Ia, in which at least one group $R^5$ is selected from the group consisting of $C_{1-6}$alkyl, phenyl, —CHR'phenyl, and —CHR'OC(=O)R", and the remaining groups $R^5$ are selected from H, $C_{1-6}$alkyl, phenyl, —CHR'phenyl and —CHR'OC(=O)R", wherein each group R' is H or $C_{1-6}$alkyl and each group R" is —$C_{1-6}$alkyl or —O$C_{1-6}$alkyl, where $C_{1-6}$alkyl and the alkyl portion of —O$C_{1-6}$alkyl may optionally be substituted with one or more substituents independently selected from 1–5 halogen atoms, a phenyl group, or a mixture of these. The phenyl group in —CHR'phenyl, the phenyl group that is an optional substituent on $C_{1-6}$alkyl and —O$C_{1-6}$alkyl, and the phenyl ester group that is obtained when $R^5$ is phenyl may optionally be substituted with 1–3 groups independently selected from halogen, —$CH_3$, —$CF_3$, —$OCH_3$ and —$OCF_3$. By this definition, the phosphonic acid group having formula Ia is a monoester or diester. Carboxy substituents that may be present as optional substituents in compounds having formula Ia may be present as $CO_2R^5$.

In preferred compounds, the groups $R^5$ that are not H may all be the same because of the difficulty of synthesizing different $R^5$ groups on the same phosphonates. In many cases, the prodrug will be a mixture of compounds having different levels of esterification on the phosphonic acid groups because of the difficulty of synthesizing and separating discrete pure compounds.

Optical Isomers—Diastereomers—Geometric Isomers

Some of the compounds described herein contain one or more asymmetric centers and may thus give rise to diastereomers and enantiomers, which in turn can be resolved as optical isomers. The present invention includes all such diastereomers and enantiomers, including racemic mixtures and resolved, enantiomerically pure forms, and pharmaceutically acceptable salts thereof. Some of the compounds described herein contain olefinic double bonds, and unless specified otherwise, include both E and Z geometric isomers.

Salts

The pharmaceutical compositions of the present invention comprise a compound of the current invention or a pharmaceutically acceptable salt thereof as an active ingredient, and may also contain a pharmaceutically acceptable carrier and optionally other therapeutic ingredients. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment or of specific compounds which follows, references to the compounds of Formula I and other formulae are meant to include the pharmaceutically acceptable salts.

Utilities

The compounds specifically exemplified herein exhibit good efficacy in inhibiting the PTP-1B enzyme, as shown by their in vitro assays. The compounds almost always have an $IC_{50}$ value of less than 2 µM in the enzyme assay described in the Assays section, and generally (and preferably) have an $IC_{50}$ value of less than 1 µM.

Inhibitors of PTP-1B improve insulin-sensitivity and may have utility in preventing or treating diabetes, improving glucose tolerance and insulin-sensitivity when there is insulin-resistance, and in treating or preventing obesity, all in mammals that are in need of such treatments or that might benefit from such treatments, including human beings. The compounds are more generally useful in treating Type 2 diabetes (non-insulin dependent diabetes, or NIDDM). The compounds may also cause a beneficial reduction in triglycerides and lipids.

Compounds that inhibit PTP-1B may also be useful in the treatment, prevention or control of a number of conditions that accompany type 2 diabetes, including hyperlipidemia, hypertriglyceridemia, hypercholesterolemia (including beneficially raising low HDL levels), atherosclerosis, vascular restenosis, pancreatitis, adipose cell tumors, adipose cell carcinomas such as liposarcoma, dyslipidemia, inflammatory bowel disease, inflammation in general, and other disorders where insulin resistance is a component. Finally, these compounds may be used to treat or prevent cancer, such as prostate cancer, neurodegenerative diseases and the like.

Pharmaceutical Compositions

For the treatment of any of these PTP-1B-mediated diseases the active compound may be administered orally, topically, parenterally, by inhalation spray or rectally in dosage units containing conventional pharmaceutically acceptable carriers. The term parenteral as used herein includes subcutaneous, intravenous, intramuscular and intrasternal injection and infusion techniques. In addition to the treatment of warm-blooded animals such as mice, rats, horses, cattle, sheep, dogs, cats, etc., the compounds of the invention are useful for the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavouring agents, colouring agents and preserving agents in order to provide pharmaceutically elegant and palatable preparations. Tablets contain the active ingredient in admixture with pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy-ethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical composition may be in the form of a sterile injectable aqueous or oleageous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent, for example as a solution in 1,3-butanediol. Examples of vehicles and solvents include water, Ringer's solution and isotonic sodium chloride. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds may also be administered in the form of suppositories. These compositions can be prepared by mixing the drug with a suitable non-irritating excipient which is solid at ordinary temperatures but molten at the body temperature and will therefore release the drug. Such materials include cocoa butter and polyethylene glycols.

For topical use, creams, ointments, gels, solutions or suspensions containing the compound are employed. (For purposes of this application, topical application includes mouth washes and gargles.) Topical formulations may include cosolvents, emulsifiers, penetration enhancers, preservatives,emollients and the like.

The pharmaceutical composition may also be further comprised of a second anti-diabetic or anti-obesity effective compound.

Dose Ranges

Dosage levels on the order of from about 0.01 mg to about 100 mg/kg of body weight per day are useful in the treatment of the above-indicated conditions, or alternatively about 0.5 mg to about 7 g per patient per day. For example, the diseases and conditions described herein may be effectively treated by the administration of from about 0.01 to 50 mg of the compound per kilogram of body weight per day, or alternatively about 0.5 mg to about 3.5 g per patient per day.

The active ingredient is typically combined with the carrier to produce a dosage form suitable for the particular patient being treated and the particular mode of administration. For example, a formulation intended for the oral administration of humans may contain from about 0.5 mg to about 5 g of the active agent, compounded with an appropriate and convenient amount of carrier material which may vary from about 5 to about 95 percent of the total composition. Representative dosage forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It is understood that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

In further aspects, the invention encompasses pharmaceutical compositions for treating PTP-1B mediated diseases as defined above comprising an effective amount of the active compound and one or more other pharmaceutically active compounds, such as anti-diabetic compounds (for example, insulin, sulfonyl ureas, PPAR-alpha and/or -gamma ligands, including ligands that have both PPAR-alpha and -gamma activity), anti-obesity compounds, and compounds that improve the lipid profile of the patient.

Thus, the methods of treatment or prevention described herein may further be comprised of administering to said patient a second anti-diabetic compound in an amount effective to treat, control, or prevent diabetes, alone or in combination with the PTP-1B inhibitors of this invention.

Similarly, the methods of treatment or prevention described herein may further be comprised of administering to said patient an anti-obesity compound in an amount effective to treat, control or prevent obesity, alone or in combination with the PTP-1B inhibitors of this invention.

Similarly, the methods of treatment of diabetes may comprise the administration of a cholesterol biosynthesis inhibitor, particularly an HMG-CoA reductase inhibitor, such as lovastatin, simvastatin, pravastatin, fluvastatin, atorvastatin and rivastatin, in an amount effective to improve the lipid profile. In combination with a PTP-1B inhibitor, this may be beneficial in treating or preventing atherosclerosis and other conditions that often are associated with Type 2 diabetes.

Examples of other pharmaceutically active compounds that may be combined with a compound of Formula I and administered in combination with the PTP-1B inhibitors include, but are not limited to, the following compounds or compositions or groups of compounds or compositions that are used as anti-diabetes compounds (a, b, c, d, f, and i below), anti-obesity compounds (g below), and/or compounds or compositions for lipid profile control (e and h below):

(a) insulin sensitizers including (i) PPARγ agonists such as the glitazones (e.g. pioglitazone, englitazone, MCC-555, rosiglitazone, and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin, pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) inhibitors of cholesterol absorption, for example beta-sitosterol and acyl CoA:cholesterol acyltransferase inhibitors, for example melinamide, and (vi) probucol;

(f) PPARα/γ agonists;

(g) antiobesity compounds such as appetite suppressants, fenfluramine, dexfenfluramine, phentiramine, subitramine, orlistat, neuropeptide Y5 inhibitors (NP Y5 receptor antagonosts), leptin, which is a peptidic hormone, $\beta_3$ adrenergic receptor agonists, and PPARγ antagonists and partial agonists;

(h) ileal bile acid transporter inhibitors; and (i) insulin receptor activators, such as those disclosed in copending, commonly assigned U.S. application Ser. Nos. 09/095,244 and 09/280,602.

Where a second pharmaceutical is used in addition to an active compound taught herein, the two pharmaceuticals may be administered together in a single composition, separately at approximately the same time, or on separate dosing schedules. The important feature is that their dosing schedules comprise a treatment plan in which the dosing schedules overlap in time and thus are being followed concurrently.

ASSAYS FOR DEMONSTRATING BIOLOGICAL ACTIVITY

Activity in the compounds of this application is demonstrated using the following assays for PTP-1B-inhibiting activity.

Phosphatase Assay Protocol

Materials:

EDTA—ethylenediaminetetraacetic acid (Sigma)

DMH—N,N'-dimethyl-N,N'-bis(mercaptoacetyl)-hydrazine (synthesis published in *J. Org. Chem.* 56, pp. 2332–2337, (1991) by R. Singh and G. M. Whitesides and can be substituted with DTT—dithiothreitol Bistris—2,2-bis(hydroxymethyl)2,2',2"-nitrilotriethanol-(Sigma) Triton X-100—octylphenolpoly(ethylene-glycolether) 10 (Pierce)

Antibody: Anti-glutathione S-transferase rabbit (H and L) fraction (Molecular Probes)

Enzyme: Human recombinant PTP-1B, containing amino acids 1–320, fused to GST enzyme (glutathione S-transferase) or to FLAG peptide purified by affinity chromatography (Huyer et al, 1997, J. Biol. Chem., 272, 843–852). Wild type contains active site cysteine(215), whereas mutant contains active site serine(215).

Tritiated peptide: Bz-NEJJ-CONH$_2$, Mwt. 808, empirical formula, $C_{32}H_{32}T_2O_{12}P_2F_4$

| Stock Solutions | |
|---|---|
| (10X) Assay Buffer | 500 mM Bistris (Sigma), pH 6.2, MW = 209.2 |
| | 20 mM EDTA (GIBCO/BRL) |
| | Store at 4° C. |

| -continued | |
|---|---|
| Prepare fresh daily: | |
| Assay Buffer (1X) (room temp.) 2 mM EDTA | 50 mM Bistris<br>5 mM DMH (MW = 208) |
| Enzyme Dilution | |
| Buffer (keep on ice) | 50 mM Bistris<br>2 mM EDTA<br>5 mM DMH<br>20% Glycerol (Sigma)<br>0.01 mg/ml Triton X-100 (Pierce) |
| Antibody Dilution | |
| Buffer (keep on ice) | 50 mM Bistris<br>2 mM EDTA |

IC$_{50}$ Binding Assay Protocol:

Compounds (ligands) which potentially inhibit the binding of a radioactive ligand to the specific phosphatase are screened in a 96-well plate format as follows:

To each well is added the following solutions @ 25° C. in the following chronological order:

1. 110 μl of assay buffer.
2. 10 μl. of 50 nM tritiated BzN-EJJ-CONH$_2$ in assay buffer (1×) @ 25° C.
3. 10 μl. of testing compound in DMSO at 10 different concentrations in serial dilution (final DMSO, about 5% v/v) in duplicate @ 25° C.
4. 10 μl. of 3.75 μg/ml purified human recombinant GST-PTP-1B in enzyme dilution buffer.
5. The plate is shaken for 2 minutes.
6. 10 μl. of 0.3 μg/ml anti-glutathione S-transferase (anti-GST) rabbit IgG (Molecular Probes) diluted in antibody dilution buffer @ 25° C.
7. The plate is shaken for 2 minutes.
8. 50 μl. of protein A-PVT SPA beads (Amersham) @ 25° C.
9. The plate is shaken for 5 minutes. The binding signal is quantified on a Microbeta 96-well plate counter.
10. The non-specific signal is defined as the enzyme-ligand binding in the absence of anti-GST antibody.
11. 100% binding activity is defined as the enzyme-ligand binding in the presence of anti-GST antibody, but in the absence of the testing ligands with the non-specific binding subtracted.
12. Percentage of inhibition is calculated accordingly.
13. IC$_{50}$ value is approximated from the non-linear regression fit with the 4-parameter/multiple sites equation (described in: "Robust Statistics", New York, Wiley, by P. J. Huber (1981) and reported in nM units.
14. Test ligands (compounds) with larger than 90% inhibition at 10 μM are defined as actives.

| Enzyme Assay PTP-1B | |
|---|---|
| Assay buffer | 50 mM Bis-Tris (pH = 6.3)<br>2 mM EDTA<br>5 mM N,N'-dimethyl-N,N'-bis(mercaptoacetyl)hydrazine (DMH) |
| Substrate | 10 mM fluorescein diphosphate (FDP) store at −20° C. |
| Enzyme dilution buffer | 50 mM Bis-Tris (pH = 6.3)<br>2 mM EDTA<br>5 mM DMH<br>20% (v/v) glycerol<br>0.01% Triton X-100 |

The assay was carried out at room temperature in 96 well plates. The reaction mixture in 170 µl contained 50 mM Bis-Tris (pH=6.3), 2 mM EDTA, 5 mM N,N'-dimethyl-N, N'bis(mercaptoacetyl)hydrazine (DMH) and 10 µM fluorescein diphosphare (FDP). 10 µl of 10 concentrations (serial dilution) of the test compound (inhibitor) dissolved in DMSO or DMSO alone for control was added to each well and the plate was mixed for 2 min. The reaction was initiated by adding 20 µl of diluted PTP-1B (50 nM in 50 mM Bis/Tris (pH=6.3), 2 mM EDTA, 5 mM DMH, 20% glycerol and 0.01% Triton X-100. The phosphatase activity was followed by monitoring the appearance of the fluorescent product fluorescein monophosphate (FMP) continuously for 15–30 min, using the Cytofluor II plate reader (PerSeptive Biosystems Inc.) with excitation of 440 nm (slit width 20 nm) and emission at 530 nm (slit width 25 nm). All the assays were done at least in duplicate. The initial rate of FMP formation is plotted against the concentration of inhibitor and the data was fitted to 4-parameter equation and the inflection point of the fit is the $IC_{50}$.

PHARMACOKINETICS IN RATS

Per Os Pharmacokinetics in Rats

Procedure:

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.

Vehicles:

The following vehicles may be used in PO rat blood level determinations:

| | |
|---|---|
| PEG 200/300/400: | restricted to 2 mL/kg |
| Methocel 0.5%–1.0%: | 10 mL/kg |
| Tween 80: | 10 mL/kg |

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv\ (mg/kg)}{AUCiv}$$

The units of CL are mL/h·kg (milliliters per hour kilogram)

Intravenous Pharmacokinetics in Rats

Procedure:

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles:

The following vehicles may be used in IV rat blood level determinations:

| | |
|---|---|
| Dextrose: | 1 mL/kg |
| 2-Hydroxypropyl-b-cyclodextrin | 1 mL/kg |
| DMSO (dimethylsulfoxide): | Restricted to a dose volume of 0.1 mL per animal |
| PEG 200: | Not more than 60% mixed with 40% sterile water - 1 mL/kg |

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv \text{ (mg/kg)}}{AUCiv}$$

The units of CL are mL/h·kg (milliliters per hour kilogram).

PTP 1B Intact Cell Assay

This assay is the subject of copending, commonly assigned U.S. Provisional Application No. 60/123,243, filed Mar. 8, 1999, which patent application is incorporated herein by reference, and was recently published in Cromlish, Wanda A., Paul Payette and Brian P. Kennedy (1999) *Biochem Pharmocol* 58: 1539–1546.

Construction of Recombinant Baculovirus Transfer Vectors and Insect Cells

Briefly, using the Bac-to-Bac Baculovirus Expression System (Gibco-BRL, Mississauga, Ontario, Canada) PTP 1B cDNA (obtained from Dr. R. L. Erikson, Harvard University, USA), is cloned into the pFASTBAC donor plasmid engineered to include a FLAG sequence at the 5' end of the cDNA (PTP1B-FL). The recombinant plasmid is transformed into competent DH10BAC *E. coli* cells. Following transposition and antibiotic selection, the recombinant bacmid DNA is isolated from selected *E. coli* colonies and used to transfect sf9 insect cells (Invitrogen, San Diego, Calif., U.S.A.). The sf9 cells are cultured in spinner flasks at 28° C. in Graces supplemented medium (Gibco-BRL, Mississauga, Ontario, Canada) with 10% heat-inactivated fetal bovine serum (Gibco-BRL) following the protocol of Summers and Smith (*A manual for Methods for Baculovirus Vectors and Insect Culture Procedures*(Bulletin No. 1555). Texas A & M University, Texas Agricultural Experiment Station, College Station, Tex., 1987).

Intact Cell Assay

Infected sf9 cells expressing PTP1B-FL and mock infected cells, are harvested at 29 hpi (hours post infection) by gentle centrifugation (Beckman GS-6R) at 460 rpm, (48 g) for 5 min. Cells are washed once in assay buffer (Hanks' solution buffered with 15 mM Hepes, pH 7.4, obtained from Sigma, St. Louis, Mo., U.S.A.) and recentrifuged at 300 rpm (21 g) for 10 min. The cells are then gently resuspended in assay buffer and examined using a hemacytometer for cell density and viability by trypan blue exclusion. Assays are performed using a Tomtec Quadra 96 pipeting robot, programmed to mix the cells gently after each addition. In 200 µL of assay buffer, $2 \times 10^5$ PTP expressing cells or mock infected cells are dispensed into each well of 96-well polypropylene plates and pre-incubated either with a test compound or DMSO vehicle (3 µL), for 15 min at 37° C. The pre-incubated cells are challenged with a final concentration of 10 mM pNPP (p-nitrophenyl phosphate, obtained from Sigma-Aldrich Canada Ltd., Oakville, Ontario) for 15 min, centrifuged at 4° C. and the amount of substrate hydrolysis is determined spectrophotometerically at $OD_{405}$.

Oral Glucose Tolerance Test

Oral glucose tolerance tests are done on conscious Zucker obese fa/fa rats or obese ob/ob mice (age 12 weeks or older). The animals are fasted for 16–18 hours before use for experiments. A test compound or a vehicle is given either intraperitoneally or orally 60 minutes before oral administration of a glucose solution at a dose of 2 g/kg body weight. Blood glucose levels are measured using a Medisense glucometer from tail bled samples taken at different time points before and after administration of glucose. A time curve of the blood glucose levels is generated and the area-under-the-curve (AUC) for 120 minutes is calculated (the time of glucose administration being time zero). Percent inhibition is determined using the AUC in the vehicle-control group as zero percent inhibition.

In separate studies, C57BL/6J mice are fed a high fat (35%) and high carbohydrate (36%) diet obtained from Bioserv (Frenchtown, N.J.) for 3 to 4 weeks, at which time the mice gained 50–100% of the baseline body weight. Oral glucose tolerance tests are done in the same manner as described above.

EXAMPLES AND SYNTHETIC METHODS

The invention is further illustrated by the following non-limiting examples. The new compounds according to this invention are summarized in Table 1. General procedures used to synthesize the compounds are summarized under the title, Methods of Synthesis. Specific intermediates and methods of making them are presented in the Synthesis of Intermediates section. Finally, the actual syntheses of the specific new compounds are presented in Examples 1–29.

TABLE 1

Structures of Examples

| | Example | Method |
|---|---|---|
| 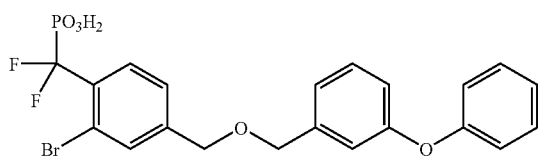 | 1 | A + B |

TABLE 1-continued

Structures of Examples

| Structure | Example | Method |
|---|---|---|
| 4-Br-C6H4-CH2-O-CH2-(3-Br,4-CF2PO3H2)C6H3 | 2 | A + B |
| 4-CO2Me-C6H4-CH2-O-CH2-(3-Br,4-CF2PO3H2)C6H3 | 3 | A + B |
| 4-SMe-C6H4-CH2-O-CH2-(3-Br,4-CF2PO3H2)C6H3 | 4 | A + B |
| 4-SO2Me-C6H4-CH2-O-CH2-(3-Br,4-CF2PO3H2)C6H3 | 5 | A + B |
| 4-F-C6H4-O-CH2-(3-Br,4-CF2PO3H2)C6H3 | 6 | A + B |
| 3-SO2Me-biphenyl-4'-CH2-O-CH2-(3-Br,4-CF2PO3H2)C6H3 | 7 | A + B |
| C6H5-CH2-O-CH2-(3-Br,4-CF2PO3H2)C6H3 | 8 | A + B |
| 3-NO2-C6H4-CH2-O-CH2-(3-Br,4-CF2PO3H2)C6H3 | 9 | A + B |

TABLE 1-continued

Structures of Examples

| Structure | Example | Method |
|---|---|---|
| (3-Br, 4-CF2PO3H2-phenyl)-CH2-O-CH2CH2-(4-Br-phenyl) | 10 | A + B |
| (3-Br, 4-CF2PO3H2-phenyl)-CH2-O-CH2CH2-phenyl | 11 | A + B |
| (3-Br, 4-CF2PO3H2-phenyl)-CH2-O-CH2CH2CH2-phenyl | 12 | A + B |
| (3-Br, 4-CF2PO3H2-phenyl)-CH2-O-CH2-CH(CH3)-phenyl | 13 | A + B |
| (3-Br, 4-CF2PO3H2-phenyl)-CH2-O-CH2CH2-(2-naphthyl) | 14 | A + B |
| (3-Br, 4-CF2PO3H2-phenyl)-CH2-O-CH2CH2-(1-naphthyl) | 15 | A + B |
| (3-Br, 4-CF2PO3H2-phenyl)-CH2-O-CH2-CH(phenyl)2 | 16 | A + B |

TABLE 1-continued

Structures of Examples

| Structure | Example | Method |
|---|---|---|
| 4-(difluoro(phosphono)methyl)-3-bromo-benzyl alcohol | 17 | C |
| 4-(difluoro(phosphono)methyl)-3-bromo-benzyl 1,2-diphenylethyl ether | 18 | D |
| 4-(difluoro(phosphono)methyl)-3-bromo-benzyl 2,3-diphenylpropyl ether | 19 | A + B |
| 4-(difluoro(phosphono)methyl)-3-bromo-benzyl 2-(4-tert-butylphenyl)ethyl ether | 20 | A + B |
| 4-(difluoro(phosphono)methyl)-3-bromo-benzyl (E)-3-(4-bromophenyl)allyl ether | 21 | A + B |
| 4-(difluoro(phosphono)methyl)-3-bromo-benzyl 2-((4-fluorobenzyl)thio)ethyl ether | 22 | A + B |
| 4-(difluoro(phosphono)methyl)-3-bromo-benzyl 3-(4-bromophenyl)propyl ether | 23 | A + B |

TABLE 1-continued

Structures of Examples

| Structure | Example | Method |
|---|---|---|
| (PO₃H₂, CF₂, Br-phenyl-CH₂-O-CH₂CH₂-phenyl-Cl) | 24 | A + B |
| (PO₃H₂, CF₂, Br-phenyl-CH₂-O-CH₂CH₂-N-phthalimide) | 25 | A + B |
| (PO₃H₂, CF₂, Br-phenyl-CH₂-O-CH₂CH₂-(2,4-dichlorophenyl)) | 26 | A + B |
| (PO₃H₂, CF₂, Br-phenyl-CH(OH)-CH₂-CH=CH₂) | 27 | E |
| (PO₃H₂, CF₂, Br-phenyl-CH₂-O-CH₂CH₂-(2-OMe-phenyl)) | 28 | A + B |
| (PO₃H₂, CF₂, Br-phenyl-CH₂-O-CH₂CH₂-(2-Br-phenyl)) | 29 | A + B |

METHODS OF SYNTHESIS

The compounds of the present invention can be prepared according to the following methods.

Method A

4-Aminobenzoic Acid II can be brominated with pyridine hydrobromide perbromide to give III which is treated with NaNO₂/HCl and KCN/CuCN to give nitrile IV. DIBAL reduction followed by bromination with POBr₃, gives VI, which is treated with lithium dialkyl phosphite to afford the phosphonate alcohol VII. Swern oxidation followed by fluorination with DAST provides the desired difluoromethyl phosphonate IX.

Method A

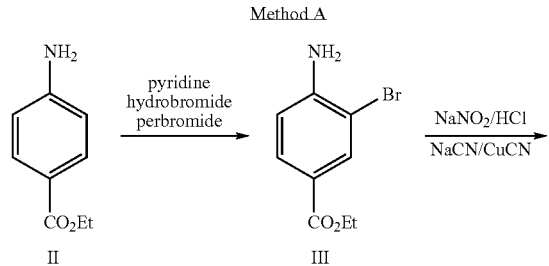

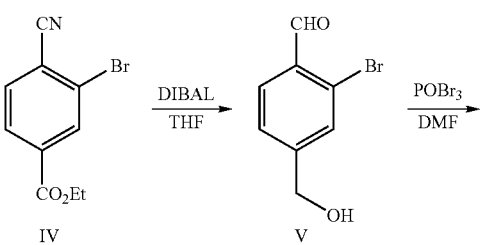

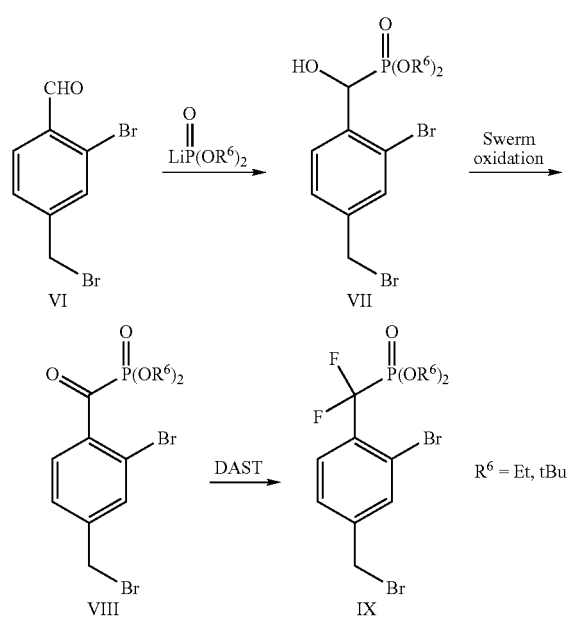

Method B

A mixture of X and HOR in a suitable solvent such as CH$_3$CN or DMF is treated with a base such as Cs$_2$CO$_3$ or NaH to give the resulting ether XI, which is deprotected to give the desired phosphonic acid I.

Method B

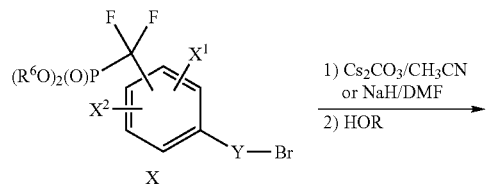

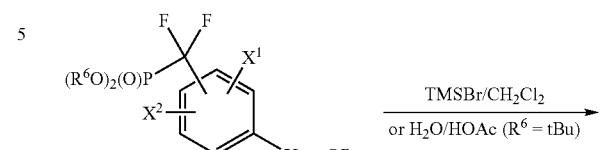

$R^6$ = Et, tBu
Y = CH$_2$

Method C

Benzyl bromide IX is treated with NMO in dioxane to give the resulting aldehyde XII which is reduced to alcohol XIII with NaBH$_4$. Cleavage of the phosphonate ester then gives phosphonic acid XIV.

Method C

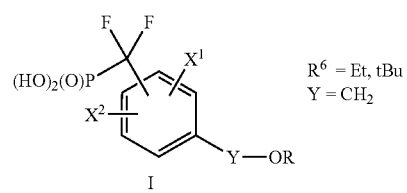

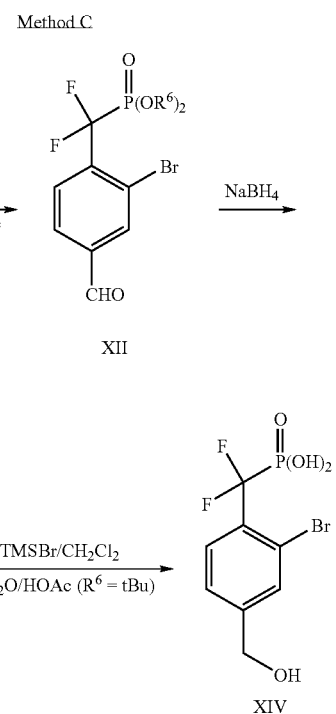

Method D

Benzyl alcohol XIII is treated with silver trifluoroacetate and desyl bromide to give ether XV. The ketone is reduced with NaBH$_4$ and the resulting secondary alcohol intermediate is treated with TFA and triethylsilane to give deoxygenated ether XVI. Deprotection of the phosphonate ester then gives the phosphonic acid XVII.

Method D

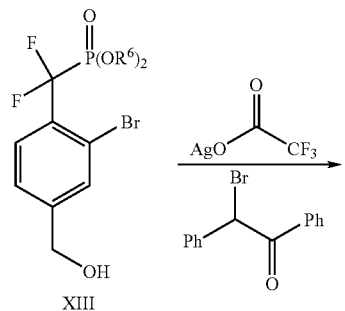

XIII

XV

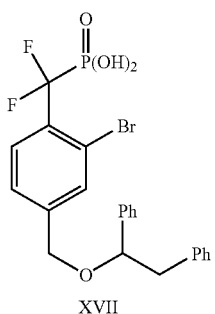

XVI

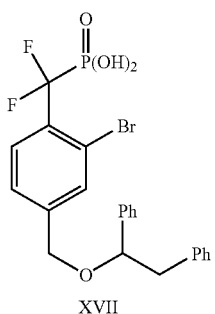

XVII

Method E

Aldehyde XII is treated with a suitable Grignard reagent such as allyl magnesium bromide to give secondary alcohol XVIII. The phosphonate ester is then cleaved to give the phosphonic acid XIX.

Method E

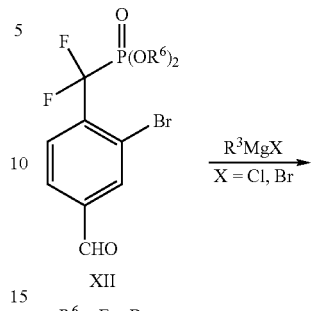

XII $R^6$ = Et, tBu

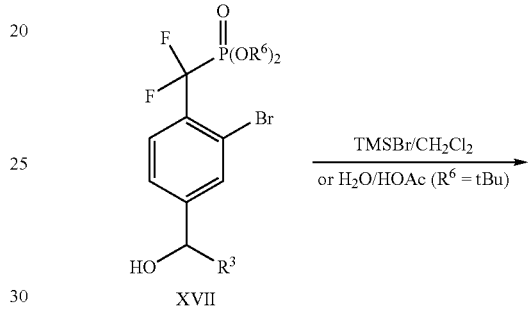

XVII

XIX

EXAMPLES

The following examples are provided to illustrate the invention. They should not be construed as limiting the scope of the invention, which is defined by the appended claims.

In the various synthetic examples:

(i) all operations were carried out at room or ambient temperature, that is, at a temperature in the range 18–25° C.;

(ii) evaporation of solvent was carried out using a rotary evaporator under reduced pressure (600–4000 pascals: 4.5–30 mm. Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s, singlet; d, doublet; t, triplet; m, multiplet; br, broad; etc. In addition "AR" signifies an aromatic signal;

(viii) chemical symbols have their usual meanings; the following abbreviations are used: v (volume), w (weight), b.p. (boiling point), m.p. (melting point), L (litre(s)), mL (millilitres), g (gram(s)), mg (milligrams(s)), mol (moles), mmol (millimoles), eq (equivalent(s)).

Example 1

(2-bromo-4-{[(3-phenoxybenzyl)oxy]methyl}phenyl)(difluoro)methylphosphonic acid

Step 1 Ethyl 4-amino-3-bromobenzoate

To a mechanically stirred solution of ethyl 4-aminobenzoate (165 g, 1 mol) in THF (1.2 L) and pyridine (200 mL) at ~10° C. was added portionwise (~10–20 g each time) of pyridine hydrobromide perbromide (tech. 90%, 365 g, 1.02 mol) over a period of 1 h. Internal temperature was kept at 10–15° C. After completion of addition, the mixture was stirred for 30 min, then filtered through celite and the filter cake was washed with THF (1 L). The filtrate was diluted with $Et_2O$, washed with 0.5 M of aqueous $NaHSO_3$ (2×, 400 mL), brine, dried ($MgSO_4$) and concentrated. The residue contained too much $H_2O$ and therefore was dissolved in EtOAc (1 L), washed with brine, dried ($MgSO_4$) and concentrated to give a semi-solid residue. The residue was swished with hexanes-$Et_2O$ (2:1) to yield 187 g (77%) of the title compound as a white powder. The mother liquor was evaporated and swished again to give 19 g (8%) of additional title compound as a light brown powder.

Step 2 Ethyl 3-bromo-4-cyanobenzoate

To a three necked 3 L round bottomed flask with a mechanical stirrer was added 3 M aqueous HCl (790 mL), followed by ethyl 4-amino-3-brombenzoate (195 g, 0.8 mol) and the mixture was stirred for 15 min. After cooling to 5° C., a solution of 4M aqueous $NaNO_2$ (240 mL, 0.96 mol) was added over a period of 30–45 min. The resulting mixture was further stirred for 30 min. and an almost homogenous solution was obtained. The mixture was filtered through glass wool to remove the insoluble residue. The solution was then added to a vigorously stirred solution of CuCN (111 g, 1.24 mol) and NaCN (162 g, 3.3 mol) in $H_2O$ (1 L) and EtOAc (500 mL) at room temperature in a 6 L Erlenmeyer flask over ~45 min. The resulting mixture was further stirred at r.t. for 30 min., filtered through celite and extracted with EtOAc. The EtOAc extract was washed with brine, 0.5 M aqueous NaOH, dried ($MgSO_4$) and concentrated. Chromatography over silica gel and elution with hexanes:EtOAc (6:1), then (3:1), swished with hexanes and small amount of $Et_2O$ to give a light brown powder. The mother liquor was concentrated and swished again. Combined yield of the title compound was 119 g (58%).

Step 3 2-Bromo-4-(hydroxymethyl)benzaldehyde

To a stirring cold (−78° C.) solution of ethyl 3-bromo-4-cyanobenzoate (0.41 mol, 104 g) in THF (2.3 L was added dropwise a solution of diisobutylaluminum hydride (2.0 mol, 1.36 L; 1.5 M in toluene) over a period of 1.5 h. After addition was completed, the mixture was warmed to rt over a period of 3 h. The mixture was then cooled to 0–5° C. and 40 ml of acetone was added slowly. The mixture was then transferred via a cannula to a cold (0° C.) stirring aqueous solution of HCl (2.2 L 3 N) over a period of 1.5 h, maintaining the temperature of the aqueous solution below 30° C. After the transfer was completed, the mixture was stirred for another 0.25 h. The organic solution was separated and the aqueous was extracted twice with EtOAc (3 L). The combined organic extracts were washed with brine, dried with $MgSO_4$ (anhyd.) and concentrated to give 74 g (83%) of the title compound as a light yellow solid.

Step 4 2-Bromo-4-(bromomethyl)benzaldehyde

To a stirring cold (0° C.) solution of $POBr_3$ (0.6 mol, 171 g) in $CH_2Cl_2$ (1.6 L) was added dropwise DMF (0.75 L) over a period of 1 h. A solution of 2-bromo-4-hydroxymethyl-benzaldehyde (0.49 mol, 107 g) in $CH_2Cl_2$ (0.75 L) was then added dropwise over a period of 0.5 h. The resulting mixture was stirred at 0° C. for another 0.5 h and was then transferred via a cannula to a cold (0° C.) stirring aqueous solution of $NaHCO_3$ (3 L, 1M) while maintaining the temperature of the aqueous solution below 10° C. After the transfer was completed, the mixture was extracted with $CH_2Cl_2$ (2 L). The organic extract was separated and washed with $H_2O$ (3 L) and brine (3 L), dried with $MgSO_4$ (anhyd.) and concentrated to give an oil. The residue was extracted with 10% EtOAc/hexane (2 L). The organic extract was washed with $H_2O$ (2×1 L), dried with $MgSO_4$ (anhyd.) and concentrated to a solid which was swished with hexane to give 154 g (~100%) of the title compound as a beige solid.

Step 5 Diethyl[2-bromo-4-(bromomethyl)phenyl](hydroxy)methylphosphonate

To a −78° C. solution of diethyl phosphite (520 mmol., 67 mL) in THF (1 L) was added dropwise LHMDS as a 1M solution in THF (510 mmol., 510 mL). The mixture was reacted for 45 minutes and then transferred via a double-tip needle into a −50 to −60° C. solution of the aldehyde (500 mmol, 139 g) in THF (1,5 L) over 1 hour. The mixture was reacted for 1 hour at −60 to −70° C. and then transferred via double-tip into a well stirred mixture of water (3 L), ice (1 L), conc. HCl (136 mL) and ethyl acetate (500 mL). The ethyl acetate layer was separated and the aqueous further extracted twice with ethyl acetate (500 mL). The combined ethyl acetate layers were washed with water, brine and evaporated to dryness. The residue was swished in hexanes and ether (20:1), filtered and dried. Yield 192 g (92%).

Step 6 Diethyl 2-bromo-4-(bromomethyl)benzoylphosphonate

To a −78° C. solution of oxalyl chloride (355 mmol, 31 mL) in dichloromethane (500 mL) was added a solution of DMSO (478 mmol., 34 mL) in dichloromethane (250 mL) over c.a. 30–45 minutes. The mixture was aged for 15 minutes during which time a solution of the alcohol (293 mmol, 122 g) in dichloromethane (250 mL) and DMSO (60 mL) was prepared (might require gentle warming). This solution was transferred dropwise into the Swern mixture over 45–60 minutes and the resulting mixture was stirred at −78° C. for 30–60 minutes. A solution of triethylamine (1.4 moles, 200 mL) in dichloromethane (200 mL) was then added and the dry ice bath was removed. The mixture was allowed to warm-up to −10° C., at which temperature it was poured slowly into a well stirred mixture of conc. HCl (300 mL), water (2.5 L) and ice (1 L). The organic layer was quickly separated and the aqueous further extracted with dichloromethane (2×250 mL). The combined dichloromethane layers were washed with water, brine, dried with MgSO$_4$ and evaporated to dryness. Yield 114 g (94%).

Step 7 Diethyl[2-bromo-4-(bromomethyl)phenyl](difluoro) methylphosphonate

To −78° C. chloroform (400 mL) was added neat DAST (1.7 mole, 208 mL, Lancaster) over about 20–30 minutes. The ketophosphonate (0.193 mole, 80 g) as a chloroform (200 mL) solution was then added over about 20–30 minutes. The −78° C. bath was removed and the mixture was allowed to warm-up to room temperature. No reaction occurred until the internal temperature reached +18° C. The mixture was reacted at +20°<T°<+25° C. for 5 hours. Then it was cooled to −30° C. and transferred using a large canula into a well stirred (mechanical) mixture of ice and water (2.5 L each) in a 10 L flask immersed in a −5° C. bath. At the end of the transfer, the internal temperature was 10° C. The reaction flask was rinsed with dichloromethane (2×150 mL). Using a pH meter to monitor the pH inside the 10 L flask, a 1:1 solution of H$_2$O and concentrated NH$_4$OH (approx. 450 mL each) was added under vigorous stirring until the pH was 9.5. The organic layer was separated and the aqueous further extracted with dichloromethane (250 mL). The combined organic layers were washed with 0.5 N HCl, brine and dried with magnesium sulphate. Removal of the solvent in vacuo left a residue which was passed on a short column of silica gel using ethyl acetate and hexanes (1:2 to 1:1) to elute the desired material. Yield 64 g (76%).

Step 8: Diethyl(2-bromo-4-{[(3-phenoxybenzyl)oxy] methyl}phenyl)(difluoro)methylphosphonate A mixture of the product from Step 7 (0.5 g, 1.15 mmol), 3-phenoxy benzyl alcohol (0.4 mL, 2.3 mmol), and Cs$_2$CO$_3$ (dried briefly under vacuum with heating)(0.75 g, 2.3 mmol) in CH$_3$CN (10 mL) was stirred ON at 50° C. The solvent was evaporated and the residue was taken up in EtOAc/H$_2$O. The organic layer was washed with H$_2$O and brine, and was then dried (MgSO$_4$), filtered, and evaporated. The crude material was purified by flash chromatography, eluting with 1:3 EtOAc:hexane to give the title compound (0.45 g).

Step 9 (2-Bromo-4-{[(3-phenoxybenzyl)oxy] methyl}phenyl)(difluoro)methylphosphonic acid To a solution of the product from Step 8 (0.45 g, 0.86 mmol) in CH$_2$Cl$_2$ (4.5 mL) was added TMSBr (1.13 mL, 8.6 mmol). After stirring ON at r.t., the mixture was concentrated under vacuum and the residue was co-evaporated with CH$_2$Cl$_2$ (2×), EtOH (2×), and acetone (2×) to give a tan-coloured syrup (0.43 g).

$^1$H NMR (CD$_3$COCD$_2$) δ 4.58–4.64 (4H, m), 6.90–6.95 (1H, m), 6.95–7.07 (3H, m), 7.10–7.18 (2H, m), 7.33–7.41 (3H, m), 7.41–7.48 (1H, m), 7.61–7.68 (1H, m), 7.68–7.72 (1H, m).

Example 2

(2-Bromo-4-{[(4-bromobenzyl)oxy]methyl}phenyl) (difluoro)methylphosphonic acid

The title compound was obtained in the same manner as Example 1, Step 8 (using 4-bromobenzyl alcohol), followed by Example 1, Step 9.

$^1$H NMR (CD$_3$COCD$_2$) δ 4.50 (2H, s), 4.53 (2H, s), 7.33–7.38 (2H, m), 7.46–7.50 (1H, m), 7.50–7.56 (2H, m), 7.62–7.68 (1H, m), 7.68–7.74 (1H, m).

Example 3

(2-bromo-4-({[4-(methoxycarbonyl)benzyl] oxy}methyl)phenyl](difluoro)methylphosphonic acid Step 1 di(tert-butyl)[2-bromo-4-(bromomethyl)phenyl](difluoro)methylphosphonate The title compound was obtained in the same manner as in Example 1 steps 5 through 7, using di-t-butyl phosphite in the place of diethyl phosphite in Step 5.

Step 2 Methyl 4-[({3-bromo-4-[[di(tert-butoxy)phosphoryl] (difluoro)methyl]benzyl}oxy)methyl]benzoate A suspension of the product from Step 1 (150 mg, 0.3 mmol), methyl 4-(hydroxymethyl)benzoate (101 mg, 0.6 mmol), and dry Cs$_2$CO$_3$ (100 mg, 0.6 mmol) in dry CH$_3$CN (3 mL) was stirred vigorously at r.t. over the weekend. The solvent was then evaporated and the residue was taken up in EtOAc/H$_2$O. The organic layer was washed with H$_2$O and brine, and was then dried (MgSO$_4$), filtered, and evaporated. Purification of the crude product was effected by flash chromatography (1:5 EtOAc:hexane) to give a colourless oil (29 mg).

Step 3 (2-bromo-4-({[4-(methoxycarbonyl)benzyl] oxy}methyl)phenyl](difluoro)methylphosphonic acid The product of Step 2 (29 mg) was dissolved in HOAc (2 mL) to which was added H$_2$O (0.2 mL). The resulting solution was stirred ON at r.t. The solvent was then evaporated and the residue was co-evaporated with toluene (3×), followed by co-evaporation with acetone (2×) to give a colourless syrup (26 mg).

$^1$H NMR (CD$_3$COCD$_2$) δ 3.87 (3H, s), 4.66 (2H, s), 4.71 (2H, s), 7.47–7.54 (3H, m), 7.62–7.67 (1H, m), 7.71–7.75 (1H, m), 7.95–8.03 (2H, m).

Example 4

[2-bromo-4-({[4-(methylsulfanyl)benzyl] oxy}methyl)phenyl](difluoro)methylphosphonic acid Step 1 Diethyl[2-bromo-4-({[4-(methylsulfanyl)-benzyl] oxy}methyl)phenyl](difluoro)methylphosphonate The compound was prepared in the same manner as in Example 1, Step 8, using (4-methylsulfanyl)phenyl)methanol.

Step 2 [2-bromo-4-({[4-(methylsulfanyl)benzyl] oxy}methyl)phenyl](difluoro)methylphosphonic acid The title compound was obtained using the procedure of Example 1, Step 9.

$^1$H NMR (CD$_3$COCD$_2$) δ 2.49 (3H, s), 4.62 (2H, s), 4.78 (2H, s), 7.21–7.28 (2H, m), 7.36–7.43 (2H, m), 7.43–7.48 (1H, m), 7.60–7.65 (1H, m), 7.68–7.74 (1H, m).

Example 5

[2-bromo-4-({[4-(methylsulfonyl)benzyl]oxy}methyl)phenyl](difluoro)methylphosphonic acid Step 1 Diethyl[2-bromo-4-({[4-(methylsulfonyl)benzyl]oxy}methyl)phenyl](difluoro)methylphosphonate To a solution of the product of Example 4, Step 1 (0.14 g, 0.28 mmol) in MeOH (6 mL) and $CH_2Cl_2$ (4 mL) at 0° C. was added a slurry of Oxone™ (0.38 g, 0.6 mmol) in $H_2O$ (2 mL). After stirring for 45 min. at 0° C., the mixture was concentrated and the residue was taken up in EtOAc/$H_2O$. The organic phase was washed with $H_2O$ and brine, and was then dried ($MgSO_4$), filtered, and evaporated. Flash chromatography (1:2 EtOAc:hexane) gave the title compound as a tan coloured syrup (109 mg).

Step 2 [2-bromo-4-({[4-(methylsulfonyl)benzyl]oxy}methyl)phenyl](difluoro)methylphosphonic acid The product of Step 1 was treated in the same way as Example 1 Step 9 to give the title compound as a syrup (108 mg).

$^1$H NMR ($CD_3COCD_2$) δ 3.10 (3H, s), 4.69 (2H, s), 4.75 (2H, s), 7.48–7.54 (1H, m), 7.62–7.68 (3H, m), 7.53–7.55 (1H, m), 7.90–7.96 (2H, m).

Example 6

{2-bromo-4-[4-fluorophenoxy]methyl)phenyl}difluoromethylphosphonic acid

Step 1 {2-Bromo-4-[4-fluorophenoxy]methyl)phenyl}difluoromethylphosphonic acid diethyl ester A mixture of (2-bromo-4-bromomethylphenyl) difluoromethylphosphonic diethyl ester (250 mg, 0.57 mmol), 4-fluorophenol (70 mg, 0.63 mmol) and $Cs_2CO_3$ (200 mg, 0.61 mmol) in DMF (5 mL) was heated at 60–70° C. for 2 h. After cooling to r.t. the mixture was diluted with $H_2O$ extracted with EtOAc. The EtOAc extract was washed with brine (2×), dried (anhydrous $MgSO_4$) and concentrated. Chromatography over silica gel and elution with hexanes:EtOAc (1.5:1) gave 150 mg (56%) of the title compound as a colorless oil.

$^1$H NMR (Acetone-d6) δ 7.86 (s, 1H), 7.68 (d, 1H), 7.61 (d, 1H), 7.05 (m, 4H), 5.20 (s, 2H), 4.22 (m, 4H), 1.29 (t, 6H).

Step 2 {2-Bromo-4-[4-fluorophenoxy]methyl)phenyl}difluoromethylphosphonic acid disodium salt A solution of above coupling product (150 mg, 0.32 mmol) and bromotrimethylsilane (0.8 mL) in $CH_2Cl_2$ (4 mL) was stirred at r.t. overnight. Volatile materials were removed in vacuo. The residue was co-evaporated with ~90% aqueous EtOH (3×) to give the acid as a gum.

$^1$H NMR (Methanol-$d_4$) δ 7.77 (s, 1H), 7.65 (d, 1H), 7.49 (d, 1H), 6.97 (m, 4H), 5.08 (s, 2H).

Example 7

[2-Bromo-4-(3'-methylsulfonyl-biphenyl-4-yl-methoxy-methyl)-phenyl]-difluoro-methyl-phosphonic acid Step 1 1-Bromo-3-methanesulfonylbenzene To a cold (0° C.) solution of 3-bromo-thioanisole (5.0 g, 24.6 mmol) in $CH_2Cl_2$ (100 mL) was added MCPBA (15 g, 50 mmol, 56% pure). The mixture was stirred at 0° C. for 2 h and warmed to rt for 4 h. $CH_2Cl_2$ (150 mL) was added, the combined organic extracts were washed with NaOH (0.2 N), then with brine, dried (anhyd. $MgSO_4$) and concentrated in vacuo to give 5.7 g (98%) of the title compound.

Step 2 (3'-Methylsulfonyl-biphenyl-4yl)-methanol

To a degassed solution of the product of step 1 (5.7 g, 24.2 mmol,), and 4-hydroxymethylphenylboronic acid (5.47 g, 36 mmol) in toluene (150 mL) was added $Pd_2(dba)_3$ (1.09 g, 1.2 mmol). The mixture was degassed and $Ph_3P$ (2.5 g, 9.6 mmol), $Et_2NH$ (2.63 g, 36 mmol), n-propanol (18 mL) and $H_2O$ (18 mL) was added. The mixture was heated to reflux for 26 h. Aqueous $NaHCO_3$ was added and the resulting mixture was extracted with EtOAc. The combined organic extracts were washed with brine, dried (anhyd. $MgSO_4$) and concentrated in vacuo. The residue was purified by chromatography on silica gel to give 6.06 g (95%) of the title compound.

Step 3 [2-Bromo-4-(3'-methylsulfonyl-biphenyl-4-yl-methoxy-methyl)-phenyl]-difluoro-methyl-phosphonic acid diethyl ester To a solution of (3'-Methylsulfonyl-biphenyl-4yl)-methanol (262 mg, 1 mmol) in dry DMF (3 mL) was added NaH (48 mg, 50% in oil, 1 mmol, ). The mixture was stirred at rt until a solution formed. The mixture was cooled to 0° C. and the bromide of Example 1 Step 7 (436 mg, 1 mmol) was added. The mixture was warmed to rt for 18 h. Aqueous $NH_4Cl$ was added, and the mixture was extracted with EtOAc. The combined organic extracts were washed with brine, dried (anhyd. $MgSO_4$) and concentrated in vacuo. The residue was purified by chromatography on silica gel to give 116 mg (19%) of the title compound.

Step 4 [2-Bromo-4-(3'-methylsulfonyl-biphenyl-4-yl-methoxy-methyl)-phenyl]-difluoro-methyl-phosphonic acid To a solution of the product of step 4 (106 mg, 0.17 mmol) in $CHCl_3$ (4 mL) was added TMSBr (260 mg, 1.7 mmol). The mixture was stirred at rt for 20 h. The solution was concentrated in vacuo. EtOH (2 mL) was added, and the mixture was stirred at rt for 0.5 h. Concentration of the EtOH solution in vacuo gave quantitatively the title compound.

$^1$H NMR (MeOH-$d_4$) δ 3.16 (s. 3H), 4.60 (s, 2H), 4.64 (s, 2H), 7.45 (m, 3H), 7.65 (m, 5H), 7.92 (d, 1H), 7.99 (d, 2H), 8.17 (d, 2H).

Example 8

{4-[(benzyloxy)methyl]-2-bromophenyl}(difluoro)methylphosphonic acid

Step 1 Diethyl{[(Benzyloxy)methyl]-2-bromophenyl}(difluoro)methylphosphonate

To benzyl alcohol (0.10 g, 0.93 mmol) in DMF at 0° C. (5 mL) were added NaH 80% in oil (0.041 g, 1.36 mmol) and diethyl [2-bromo-4-(bromomethyl)phenyl](difluoro)methyl phosphonate (0.36 g, 0.82 mmole). After a period of 3 h at r.t., the reaction mixture was partitioned between $NH_4OAc$ solution and EtOAc. The organic phase was separated, dried over $NaSO_4$, filtered and evaporated under reduced pressure. After purification by flash chromatography the title compound was obtained (0.13 g).

Step 2 {4-[(benzyloxy)methyl]-2-bromophenyl}(difluoro)methylphosphonic acid

The compound of Step 1 (0.13 g, 0.28 mol) in $CH_2Cl_2$ (2.0 mL) was added an excess of TMSBr. After a period of 18 h, the solvents were eveporated and the crude product was co-evaporated with 3× EtOH followed by 3× toluene.

$^1$H NMR (400 MHz, Acetone-D$_6$) δ 4.60 (4H, s), 7.0–7.90 (8H, m).

Example 9

(2-bromo-4-{[(3-nitrobenzyl)oxy]methyl}phenyl)(difluoro)methylphosphonic acid

The title compound was prepared as described in Example 1 Step 8 (using 3-nitrobenzyl alcohol) followed by Example 1 Step 9.

$^1$H NMR (400 MHz, Acetone-D$_6$) δ 4.72 (s, 2H), 4.8 (s, 2H), 7.5 (d, 1H), 7.65 (m, 2H), 7.74 (s, 1H), 7.85 (d, 1H), 8.15 (d, 1H), 8.25 (s, 1H).

Example 10

(2-bromo-4-{[(2-(4-bromophenyl)ethoxy]methyl}phenyl)(difluoro)methylphosphonic acid The title compound was prepared as described in Example 1 Step 8 (using 2-(4-bromophenyl)ethanol), followed by Example 1 Step 9.

$^1$H NMR (400 MHz, Acetone-D$_6$) δ 2.95 (t, 2H), 3.75 (2H, t), 4.6 (2H, s), 7.28 (2H, d), 7.42 (d, 1H), 7.48 (d, 2H), 7.62 (2H, m).

Example 11

(2-bromo-4-[(2-phenylethoxy)methyl]phenyl}(difluoro)methylphosphonic acid

Step 1 Diethyl{2-bromo-4-[(2-phenylethoxy)methyl]phenyl}(difluoro)methylphosphonate The title compound was prepared in the same manner as described in Example 1, Step 8, using phenethyl alcohol as nucleophile.

Step 2 (2-bromo-4-[(2-phenylethoxy)methyl]phenyl}(difluoro)methylphosphonic acid The compound of Step 1 was treated as described in Example 1 Step 9.

$^1$H NMR (400 MHz, Acetone-D$_6$) δ 3.20 (2H, m), 3.60 (2H, m), 4.05 (1H, m), 7.05–7.70 (13H, m).

Example 12

{2-bromo-4-[(3-phenylpropoxy)methyl]phenyl}(difluoro)methylphosphonic acid

The title compound was prepared as described in Example 1 Step 8 (using 3-phenyl-1-propanol), followed by Example 1 Step 9.

$^1$H NMR (400 MHz, Acetone-D$_6$) δ 1.90 (2H, m), 2.80 (2H, t), 3.50 (2H, t), 4.60 (2H, s), 7.10–7.80 (8H, m).

Example 13

{2-bromo-4-[(2-phenylpropoxy)methyl]phenyl}(difluoro)methylphosphonic acid

The title compound was prepared a described in Example 1 Step 8 (using 2-phenyl-1-propanol) followed by Example 1 Step 9.

$^1$H NMR (400 MHz, Acetone-D$_6$) δ 1.30 (3H, d), 3.10 (1H, m), 4.60 (2H, m), 4.50 (2H, s), 7.10–7.70 (8H, m).

Example 14

(2-bromo-4-{[2-(2-napthyl)ethoxy)methyl}phenyl)(difluoro)methylphosphonic acid

The title compound was prepared as described in Example 1 Step 8 (using 2-napthalene ethanol) followed by Example 1 Step 9.

$^1$H NMR (400 MHz, Acetone-D$_6$) δ 3.10 (2H, t), 3.90 (2H, t), 4.60 (2H, s), 7.10–7.90 (10H, m).

Example 15

(2-bromo-4-{[2-(1-naphthyl)ethoxy]methyl}phenyl)(difluoro)methylphosphonic acid

The title compound was prepared as described in Example 1, Step 8 (using 1-napthalene ethanol), followed by Example 1, Step 9.

$^1$H NMR (400 MHz, Acetone-D$_6$) δ 3.40 (2H, t), 3.90 (2H, t), 4.60 (2H, s), 7.10–8.20 (10H, m).

Example 16

{2-bromo-4-[(2,2-diphenylethoxy)methyl]phenyl(difluoro)methylphosphonic acid

The title compound was prepared as described in Example 1 Step 8 (using 2,2-diphenylethanol), followed by Example 1 Step 9.

$^1$H NMR (400 MHz, Acetone-D$_6$) δ 4.15 (2H, d), 4.40 (1H, t), 4.60 (2H, s), 7.10 to 7.60 (13H, m).

Example 17

[2-Bromo-4-(hydroxymethyl)phenyl](difluoro)methylphosphonic acid

Step 1 diethyl (2-bromo-4-formylphenyl)(difluoro)methylphosphonate

A solution of diethyl[2-bromo-4-(bromomethyl)phenyl](difluoro)methylphosphonate (Example 1, Step 7) and NMO (3.0 g) in dioxane (0.1 M) was heated at 30° C. for 0.5 h. The reaction mixture was then partitioned between EtOAc and H$_2$O. The organic phase was separated, dried over NaSO$_4$, filtered and evaporated under reduced pressure. The title compound was purified by flash chromatography.

Step 2 diethyl[2-bromo-4-(hydroxymethyl)phenyl](difluoro)methylphosphonate

To the compound of Step 1 in EtOAc was added an excess of NaBH$_4$. The reaction mixture was poured over NH$_4$Cl saturated and EtOAc. The organic phase was separated, dried over NaSO$_4$, filtered and evaporated under reduced pressure. The title compound was purified by flash chromatography.

Step 3 [2-bromo-4-(hydroxymethyl)phenyl](difluoro)methylphosphonic acid

The title compound was prepared as described in Example 1 Step 9.

$^1$H NMR (400 MHz, CD$_3$COCD$_3$) δ 4.70 (2H, s), 7.45 (1H, d), 7.70 (1H, d), 7.80 (1H, s)

Example 18

{2-bromo-4-[(1,2-diphenylethoxy)methyl]phenyl}(difluoro)methylphosphonic acid

Step 1 diethyl{2-bromo-4-[(2-oxo-1,2-diphenylethoxy)methyl]phenyl}(difluoro)methylphosphonate A mixture of the alcohol of Example 17 Step 2, desyl bromide (1.5 g) and AgOCOCF$_3$ (1.5 g) in CH$_2$Cl$_2$ (0.06 M) was stirred at room temperature for 2 h. The reaction mixture was filtered over celite, evaporated and purified by flash chromatography to provide the title compound.

Step 2 diethyl{2-bromo-4-[(2-hydroxy-1,2-diphenylethoxy)methyl]phenyl}(difluoro)methylphosphonate To the compound of Step 1 in EtOH was added NaBH$_4$ at 0° C. After a period of 0.5 h, the reaction mixture was poured over saturated NH$_4$Cl and EtOAc. The organic phase was separated, dried over NaSO$_4$, filtered and evaporated and purified by flash chromatography, to afford the title compound.

Step 3 diethyl{2-bromo-4-[(1,2-diphenylethoxy)methyl]phenyl}(difluoro)methylphosphonate To the compound of Step 4 was added TFA and Et$_3$SiH. After a period of 18 h, the reaction mixture was evaporated under reduced pressure and purified by flash chromatography.

Step 4 {2-bromo-4-[(1,2-diphenylethoxy)methyl]phenyl}(difluoro)methylphosphonic acid The title compound was prepared as described in Example 1, Step 9.

$^1$H NMR (400 MHz, CD$_3$COCD$_3$) δ 4.05 (2H, m), 4.40 (1H, t), 4.60 (2H, s), 7.15–7.80 (13H, m).

Example 19

{2-bromo-4-[(2,3-diphenylpropoxy)methyl]phenyl}(difluoro)methylphosphonic acid

The title compound was prepared as described in Example 1 Step 8 (using 2,3-diphenyl-propan-1-ol), followed by Example 1, Step 9.

$^1$H NMR (400 MHz, CD$_3$COCD$_3$) δ 3.10 (2H, m), 3.30 (1H, m), 3.85 (2H, m), 4.55 (2H, m), 7.10–7.70 (13H, m).

Example 20

[2-bromo-4-({[4-(tert-butyl)phenethyl]oxy}methyl)phenyl](difluoro)methylphosphonic acid The title compound was prepared as described in Example 1 Step 8 (using 4-tert-butyl phenethyl alcohol), followed by Example 1, Step 9.

$^1$H NMR (400 MHz, CD$_3$COCD$_3$) δ 1.30 (9H, s), 2.90 (2H, t), 3.60 (2H, s), 3.80 (2H, t), 7.20–7.70 (7H, m).

Example 21

[2-bromo-4-({[(E)-3-(4-bromophenyl)-2-propenyl]oxy}methyl)phenyl](difluoro)methylphosphonic acid The title compound was prepared as described in Example 1 Step 8 using (E)-3-(4-bromophenyl)-2-propan-1-ol), followed by Example 1 Step 9.

$^1$H NMR (400 MHz, CD$_3$CD$_3$) δ 4.20 (2H, m), 4.55 (2H, m), 6.30 (1H, m), 6.65 (1H, m), 7.30–8.10 (7H, m), (sodium salt).

Example 22

[2-bromo-4-({2-[(4-fluorobenzyl)sulfanyl]ethoxy}methyl)phenyl](difluoro)methylphosphonic acid The title compound was prepared as described in Example 1 Step 8 (using 2-((4-fluorobenzyl)sulfanyl)ethanol), followed by Example 1 Step 9.

$^1$H NMR (acetone d$_6$) δ 2.7 (2H, m), 3.65 (2H, m), 3.8 (2H, s), 4.58 (2H, s), 7.08 (2H, m), 7.4 (3H, m), 7.7 (2H, m).

Example 23

(2-Bromo-4-{[3-(4-bromophenyl)propoxy]methyl}phenyl)(difluoro)methylphosphonic acid The diethyl ester of Example 21 was treated with H$_2$ (1 atm.) and Pd/C (5%) in EtOAc for 10 min. After filtration over celite, evaporation followed by deprotection as described in Example 1 Step 9. The title compound was obtained.

$^1$H NMR (400 MHz, CD$_3$COCD$_3$) δ 1.95 (2H, m), 2.75 (2H, m), 3.55 (2H, m), 4.55 (2H, s), 7.20–7.80 (7H, m).

Example 24

(2-bromo-4-{[(4-chlorophenethyl)oxy]methyl}phenyl)(difluoro)methylphosphonic acid The title compound was prepared as described in Example 1 Step 8 (using 4-chloro phenethyl alcohol), followed by Example 1 Step 9.

$^1$H NMR (400 MHz, CD$_3$COCD$_3$) δ 3.00 (2H, s), 3.80 (2H, t), 4.60 (2H, s), 7.10–7.70 (7H, m).

Example 25

(2-Bromo-4-{[2-(1,3-dioxo-1,3-dihydro-2H-isoindol-2-yl)ethoxy]methyl}phenyl)(difluoro)methylphosphonic acid The title compound was prepared as described in Example 1 Step 8 (using N-(2-hydroxyethyl)phthalimide and NaH in DMF), followed by Example 1, Step 9.

$^1$H NMR (400 MHz, CD$_3$COCD$_3$) δ 3.80 (2H, t), 4.00 (2H, t), 4.60 (2H, s), 7.30–7.90 (7H, m).

Example 26

(2-bromo-4-{[2-(2-(2,4-dichlorophenyl)ethoxy]methyl}phenyl)(difluoro)methylphosphonic acid The title compound was prepared as described in Example 1, Step 8, using 2(2,4-dichlorophenyl)ethanol, followed by Example 1, Step 9.

$^1$H NMR (acetone d$_6$) δ 3.07–3.12 (2H, m)m 3.78–3.83 (2H, m), 4.59–4.63 (2H, m), 7.32–7.35 (1H, m), 7.39–7.43 (1H, m), 7.45–7.49 (2H, m), 7.61–7.67 (2H, m).

Example 27

[2-bromo-4-(1-hydroxy-3-butenyl)phenyl](difluoro)methylphosphonic acid

Step 1 diethyl[2-bromo-4-(1-hydroxy-3-butenyl)phenyl](difluoro)methylphosphonate To diethyl (2-bromo-4-formylphenyl)(difluoro) methyl phosphonate (Example 17, Step 1) (0.22 g, 6.59 mmole) in ether (5 ml) at 0° C. was added allyl magnesium bromide (0.59 ml of 1M or 0.59 mmole). Then the reaction was warmed up to room temperature for 1 hour. The reaction mixture was quenched with a saturated solution of $NH_4Cl$ and extracted with ethylacetate. The extract were dried over $Na_2SO_4$ and evaporated. The residue was purified by chromatography to yield the title compound.

Step 2 [2-bromo-4-(1-hydroxy-3-butenyl)phenyl](difluoro)methylphosphonic acid

The title compound was obtained using the procedure of Example 1, Step 9.

$^1$H NMR (acetone $d_6$) δ 2.52 (2H, m), 4.8 (1H, m), 5.05 (2H, m), 5.85 (1H, m), 7.5 (1H, d), 7.65 (1H, d), 7.75 (1H, s).

Example 28

(2-bromo-4-{[2-(2-methoxyphenyl)ethoxy]methyl}phenyl)(difluoro)methylphosphonic acid The title compound was prepared as described in Example 1 Step 8 using 2-(2-methoxyphenyl)ethanol, followed by Example 1 Step 9.

$^1$H NMR (acetone $d_6$) δ 2.93–2.98 (2H, m), 3.69–3.74 (2H, m), 3.82 (3H, s), 4.58 (2H, s), 6.85–6.90 (1H, m), 6.93–6.97 (1H, m), 7.18–7.24 (2H, m), 7.37–7.42 (1H, m), 7.62–7.68 (2H, m).

Example 29

(2-bromo-4-{[2-(2-bromophenyl)ethoxy]methyl}phenyl)(difluoro)methylphosphonic acid The title compound was prepared as described in Example 1 Step 8 using 2-(2-bromophenyl)ethanol, followed by Example 1 Step 9.

$^1$H NMR (acetone $d_6$) δ 3.10–3.15 (2H, m), 3.77–3.83 (2H, m), 4.62 (2H, s), 7.16–7.21 (1H, m), 7.32–7.36 (1H, m), 7.40–7.45 (2H, m), 7.58–7.62 (1H, m), 7.63–7.69 (2H, m).

What is claimed is:

1. A compound represented by formula I:

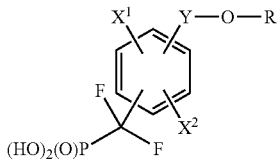

or a pharmaceutically acceptable salt or prodrug thereof, wherein:

$X^1$ is selected from the group consisting of: halogen, CN, $CO_2H$, $CO_2C_{1-6}$alkyl, $CO_2C_{2-6}$alkenyl, $OC_{1-6}$alkyl, $OC_{2-6}$alkenyl, $C(O)C_{1-6}$alkyl, $C(O)C_{2-6}$alkenyl, $OC(O)C_{1-6}$alkyl, $OC(O)C_{2-6}$alkenyl, $C_{1-6}$alkyl, $C_{2-6}$alkenyl, $S(O)_2NR^1R^2$, $C(O)NR^1R^2$, and $NR^1R^2$, wherein each alkyl group and each alkenyl group in each substituent is optionally substituted with 1–7 groups independently selected from (a) 1–5 halogen atoms and (b) 1–2 substituents independently selected from $OC_{1-3}$alkyl, $C(O)C_{1-3}$alkyl, $OC(O)C_{1-3}$alkyl, $CO_2H$, and $CO_2C_{1-3}$alkyl;

$X^2$ is selected from the group consisting of: H, OH, halogen, CN, $CO_2H$, $CO_2C_{1-6}$alkyl, $CO_2C_{2-6}$alkenyl, $OC_{1-6}$alkyl, $OC_{2-6}$alkenyl, $C(O)C_{1-6}$alkyl, $C(O)C_{2-6}$alkenyl, $OC(O)C_{1-6}$alkyl, $OC(O)C_{2-6}$alkenyl, $C_{1-6}$alkyl, $C_{2-6}$alkenyl, $S(O)_2NR^1R^2$, $C(O)NR^1R^2$, and $NR^1R^2$, wherein each alkyl group and each alkenyl group in each substituent is optionally substituted with 1–7 groups independently selected from (a) 1–5 halogen atoms and (b) 1–2 substituents independently selected from $OC_{1-3}$alkyl, $C(O)C_{1-3}$alkyl, $OC(O)C_{1-3}$alkyl, $CO_2H$, and $CO_2C_{1-3}$alkyl;

$R^1$ and $R^2$ are each independently selected from the group consisting of H and $C_{1-6}$alkyl, wherein said alkyl substituents are optionally substituted with 1–5 halogen atoms;

Alkyl, alkenyl, alkadienyl and alkynyl are linear or branched hydrocarbon structures, except where otherwise defined, containing the indicated number of carbon atoms and being substituted as indicated;

$X^1$, $X^2$, $CF_2P(O)(OH)_2$ and Y—O—R are each substituted onto any position of the aromatic ring;

Y is a $C_{1-4}$alkylene group, wherein said alkylene group is linear and optionally has one double bond or one triple bond connecting two adjacent carbon atoms, wherein each carbon of said $C_{1-4}$alkylene group independently may have one optional substituent independently selected from the group consisting of $C_{1-4}$alkyl, $C_{2-4}$alkenyl, $C_{2-4}$alkynyl, and halogen, said $C_{1-4}$alkyl, $C_{2-4}$alkenyl, and $C_{2-4}$alkynyl substituents being optionally substituted with 1–3 halogens;

R is selected from H, $C_{1-6}$alkyl, and an aromatic group selected from phenyl, naphthyl, and biphenyl, wherein $C_{1-6}$alkyl is linear and optionally has one double bond, one triple bond or one S atom connecting two adjacent carbon atoms, wherein each carbon of said $C_{1-6}$alkyl group independently may have one optional substituent selected from the group consisting of $C_{1-4}$alkyl, $C_{2-4}$alkenyl, $C_{2-4}$alkynyl, halogen, phenyl, naphthyl, biphenyl and phthalimide, said $C_{1-4}$alkyl, $C_{2-4}$alkenyl, and $C_{2-4}$alkynyl substituents being optionally substituted with 1–4 substituents independently selected from 1–3 halogens and one aromatic group selected from phenyl, naphthyl, and biphenyl, wherein R comprises 0–2 aromatic substituents, wherein said aromatic substituents optionally may be substituted onto the same carbon atom of alkyl, alkenyl and alkynyl when there are two aromatic substituents, and wherein said 0–2 aromatic groups that are substituents on R when R is $C_{1-6}$ alkyl are optionally substituted with 1–5 substituents independently selected from halogen, $C_{1-4}$alkyl, $C_{2-4}$alkenyl, $C_{2-4}$alkynyl, $OC_{1-4}$alkyl, $OC_{2-4}$alkenyl, $OC_{2-4}$alkynyl, phenoxy, $CO_2H$, $CO_2C_{1-4}$ alkyl, $SC_{1-4}$alkyl, $S(O)C_{1-4}$alkyl, $S(O)_2C_{1-4}$alkyl, $NO_2$ and CN, wherein said alkyl, alkenyl, alkynyl, Oalkyl, Oalkenyl, Oalkynyl and phenoxy substituents are optionally substituted with 1–5 halogens, and wherein when R is an aromatic group, said aromatic group is optionally substituted with 1–5 substituents selected from halogen, $C_{1-4}$alkyl, $C_{2-4}$alkenyl, $C_{2-4}$alkynyl, $OC_{1-4}$alkyl, $OC_{2-4}$alkenyl, $OC_{2-4}$alkynyl, phenoxy, $CO_2H$, $CO_2C_{1-4}$ alkyl, $SC_{1-4}$alkyl, $S(O)C_{1-4}$alkyl, $S(O)_2$ $C_{1-4}$alkyl, $NO_2$ and CN, wherein said alkyl, alkenyl, alkynyl, Oalkyl, Oalkenyl, Oalkynyl and phenoxy substituents are optionally substituted with 1–5 halogens.

2. The compound as recited in claim 1, wherein $X^1$ is ortho to the group $CF_2PO(OH)_2$; $X^1$ is selected from the group consisting of Cl, Br, $CH_3$, $OCH_3$, $CF_3$, $OCF_3$, and OH, and $X^2$ is selected from the group consisting of H, Cl, Br, $CH_3$, $OCH_3$, $CF_3$, $OCF_3$, and OH.

3. The compound as recited in claim 1, wherein $X^1$ is Br and $X^2$ is H.

4. The compound as recited in claim 1, wherein Y is $CH_2$.

5. The compound as recited in claim 1, wherein $X^1$ is Br, $X^2$ is H, Y is $CH_2$, and $X^1$ is ortho to $CF_2PO(OH)_2$.

6. The compound as recited in claim 1, wherein R is selected from $C_{1-6}$alkyl and phenyl, wherein phenyl is optionally substituted with 1–3 halogens, wherein $C_{1-6}$alkyl is linear and optionally has one double bond, one triple bond or one S atom connecting two adjacent carbon atoms, wherein $C_{1-6}$alkyl is optionally substituted with 1–2 groups independently selected from phenyl, phthalimide, naphthyl and biphenyl, wherein phenyl, naphthyl, phthalimide, and biphenyl are optionally substituted with 1–3 groups independently selected from halogen, $C_{1-4}$alkyl, phenyl, phenoxy, $SC_{1-4}$alkyl, $S(O)_2C_{1-4}$alkyl, $NO_2$, and $CO_2C_{1-4}$alkyl, wherein $C_{1-6}$alkyl, $SC_{1-4}$alkyl, $S(O)_2C_{1-4}$alkyl, and $CO_2C_{1-4}$alkyl are linear or branched and are optionally substituted with 1–3 halogens.

7. The compound as recited in claim 1, wherein
$X^1$ is Br and is ortho to $CF_2PO(OH)_2$;
$X^2$ is H;
Y is $CH_2$; and
R is selected from phenyl and $C_{1-3}$alkyl, wherein phenyl is optionally substituted with 1–3 halogens, and $C_{1-3}$alkyl is linear and optionally has one double bond, one triple bond or one S atom connecting two adjacent carbon atoms, wherein $C_{1-3}$alkyl is optionally substituted with 1–2 groups independently selected from phenyl, phthalimide, naphthyl and biphenyl, wherein phenyl, naphthyl, phthalimide, and biphenyl are optionally substituted with 1–3 groups independently selected from halogen, $C_{1-6}$alkyl, phenyl, phenoxy, $SC_{1-4}$alkyl, $S(O)_2C_{1-4}$alkyl, $NO_2$, and $CO_2C_{1-4}$alkyl, wherein $C_{1-6}$alkyl, $SC_{1-4}$alkyl, $S(O)_2C_{1-4}$alkyl, and $CO_2C_{1-4}$alkyl are linear or branched and are optionally substituted with 1–3 halogens.

8. A pharmaceutical composition which is comprised of a compound in accordance with claim 1 in combination with a pharmaceutically acceptable carrier.

9. A pharmaceutical composition in accordance with claim 8 further comprising a second anti-diabetic or anti-obesity effective compound.

10. A method of treating or controlling diabetes and complications thereof in a mammalian patient in need of such treatment comprising administering to said patient an anti-diabetic effective amount of a compound in accordance with claim 1.

11. A method of treating or controlling obesity in a mammalian patient in need of such treatment comprising administering to said patient an anti-obesity effective amount of a compound in accordance with claim 1.

12. A method in accordance with claim 10, further comprising administering to said patient an effective amount of a second compound selected from the group consisting of:
(a) insulin sensitizers, PPAR-gamma agonists, partial agonists, and antagonists, PPAR-alpha agonists, PPAR-delta agonists, and biguanides;
(b) insulin and insulin mimetics;
(c) sulfonylureas;
(d) α-glucosidase inhibitors;
(e) cholesterol lowering agents selected from the group consisting of (i) HMG-CoA reductase inhibitors; (ii) sequestrants, (iii) nicotinyl alcohol, nicotinic acid and salts thereof, (iv) PPARα agonists, (v) inhibitors of cholesterol absorption; and (vi) probucol;
(f) PPARα/γ agonists;
(g) antiobesity compounds selected from the group consisting of appetite suppressants, fenfluramine, dexfenfluramine, phentiramine, subitramine, orlistat, neuropeptide Y5 inhibitors (NP Y5 receptor antagonosts), leptin, $β_3$ adrenergic receptor agonists, and PPARγ antagonists and partial agonists;
(h) ileal bile acid transporter inhibitors; and
(i) insulin receptor activators.

13. A pharmaceutical composition in accordance with claim 8 further comprising an HMG-CoA reductase inhibitor.

14. A method for treating or controlling atherosclerosis in a mammalian patient in need of such treatment comprising administering to said patient an effective amount of a compound of claim 1 and an effective amount of an HMG-CoA reductase inhibitor.

15. A method for treating or controlling one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said method comprising the administration of an effective amount of a compound of claim 1.

16. A method of treating or controlling one or more diseases or conditions, selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said method comprising the administration of an effective amount of a compound of claim 1 and the administration of an effective amount of one or more pharmaceutically active compounds selected from the group consisting of an HMG-CoA reductase inhibitor, an anti-obesity agent, and an antidiabetic compound.

17. A pharmaceutical composition comprising (1) the compound of claim 1, (2) one or more pharmaceutically active compounds selected from the group consisting of an HMG-CoA reductase inhibitor, an anti-obesity agent, and an anti-diabetic agent, and (3) a pharmaceutically acceptable carrier.

18. A pharmaceutical composition comprising:
(1) a compound of claim 1,
(2) one or pharmaceutically active compounds selected from the group consisting of:
(a) insulin sensitizers, PPAR-gamma agonists, partial agonists, and antagonists, PPAR-alpha agonists, PPAR-delta agonsts, and biguanides;
(b) insulin and insulin mimetics;
(c) sulfonylureas;
(d) α-glucosidase inhibitors;
(e) cholesterol lowering agents selected from the group consisting of (i) HMG-CoA reductase inhibitors; (ii) sequestrants, (iii) nicotinyl alcohol, nicotinic acid and salts thereof, (iv) PPARα agonists, (v) inhibitors of cholesterol absorption; and (vi) probucol;
(f) PPARα/γ agonists;
(g) antiobesity compounds selected from the group consisting of appetite suppressants, fenfluramine, dexfenfluramine, phentiramine, sulbitramine, orlistat, neuropeptide Y5 inhibitors (NP Y5 receptor antagonosts), leptin, β₃ adrenergic receptor agonists, and PPARγ antagonists and partial agonists;

(h) ileal bile acid transporter inhibitors; and (i) insulin receptor activators; and (3) a pharmaceutically acceptable carrier.

19. A compund having a structure below, or a pharmaceutically acceptable salt thereof:

| | Example |
|---|---|
| 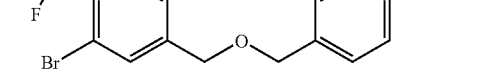 | 1, |
|  | 2, |
|  | 3, |
| 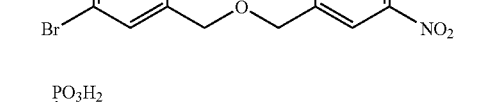 | 4, |
|  | 5, |
| 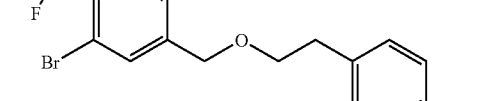 | 6, |
|  | 7, |

-continued

| | Example |
|---|---|
|  | 8, |
| 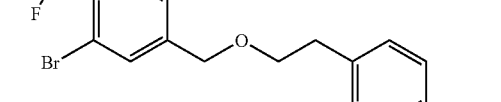 | 9, |
|  | 10, |
|  | 11, |
| 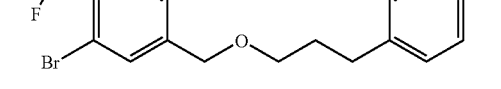 | 12, |
| | 13, |
| | 14, |

-continued
| | Example |
|---|---|
| 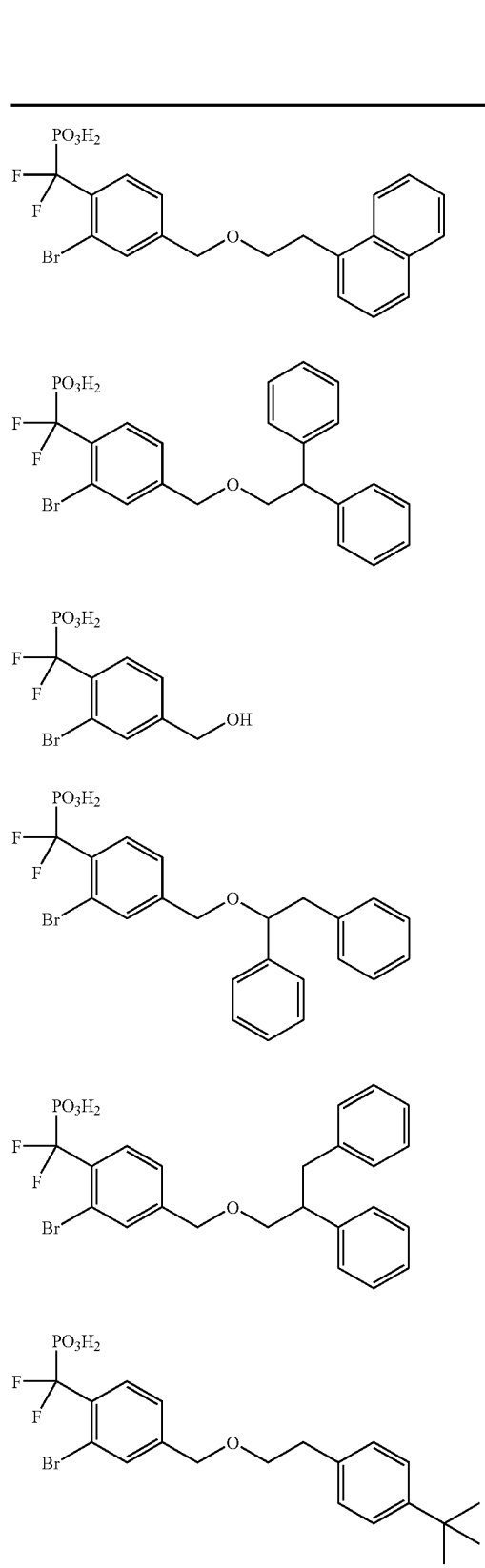 | 15, 16, 17, 18, 19, 20, |
-continued
| | Example |
|---|---|
| 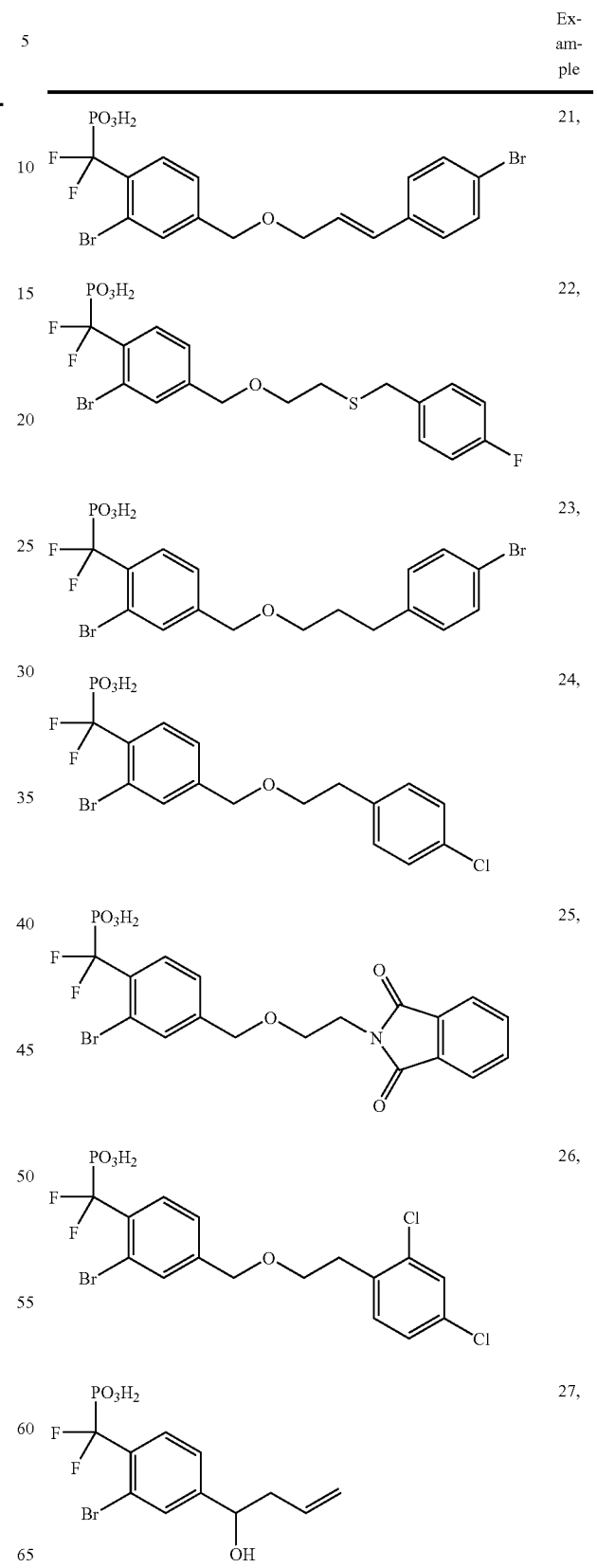 | 21, 22, 23, 24, 25, 26, 27, |

| -continued | |
|---|---|
| 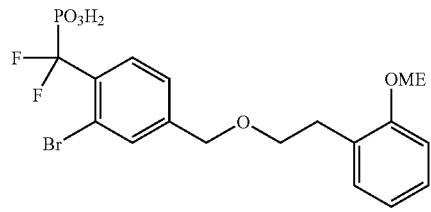 | Example 28, and |
| -continued | |
|---|---|
| 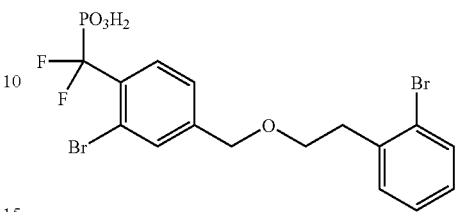 | Example 29. |
* * * * *